US006789546B2

(12) United States Patent
Reznick et al.

(10) Patent No.: US 6,789,546 B2
(45) Date of Patent: Sep. 14, 2004

(54) FILTERS FOR PREVENTING OR REDUCING TOBACCO SMOKE-ASSOCIATED INJURY IN THE AERODIGESTIVE TRACT OF A SUBJECT

(75) Inventors: Abraham Z. Reznick, Nofit (IL); Rafael M. Nagler, Timrat (IL); Ifat Klein, Galil Elion (IL)

(73) Assignee: Technion Research & Development Foundation Ltd., Haifa (IL)

( * ) Notice: Subject to any disclaimer, the term of this patent is extended or adjusted under 35 U.S.C. 154(b) by 0 days.

(21) Appl. No.: 09/987,688

(22) Filed: Nov. 15, 2001

(65) Prior Publication Data

US 2003/0031630 A1 Feb. 13, 2003

Related U.S. Application Data

(60) Provisional application No. 60/304,402, filed on Jul. 12, 2001, and provisional application No. 60/300,443, filed on Jun. 26, 2001.

(51) Int. Cl.⁷ ............................................. A24B 15/18
(52) U.S. Cl. ..................................... 131/334; 131/331
(58) Field of Search ................................ 131/202, 331, 131/334, 342, 332, 200, 201

(56) References Cited

U.S. PATENT DOCUMENTS

| 3,339,558 | A | * | 9/1967 | Waterbury .................. 131/335 |
| 3,901,248 | A | | 8/1975 | Lichtneckert et al. |
| 5,060,672 | A | | 10/1991 | Irimi et al. |
| 5,829,449 | A | | 11/1998 | Hersh |
| 5,906,811 | A | | 5/1999 | Hersh |
| 5,909,736 | A | * | 6/1999 | Stavridis et al. ............ 131/331 |
| 5,922,346 | A | | 7/1999 | Hersh |
| 6,145,511 | A | * | 11/2000 | Teufel et al. ............... 131/334 |
| 6,228,347 | B1 | | 5/2001 | Hersh |

* cited by examiner

Primary Examiner—Dionne A. Walls
(74) Attorney, Agent, or Firm—G. E. Ehrlich (1995) Ltd.

(57) ABSTRACT

A method of preventing or reducing tobacco smoke-associated injury in the aerodigestive tract of a subject is disclosed. The method comprises administering a therapeutically effective amount of an antioxidant agent capable of preventing or reducing tobacco smoke-associated injury in the aerodigestive tract of a subject.

23 Claims, 20 Drawing Sheets

FILTERS FOR PREVENTING OR REDUCING TOBACCO SMOKE-ASSOCIATED INJURY IN THE AERODIGESTIVE TRACT OF A SUBJECT

This application claims the benefit of priority of U.S. provisional patent application No. 60/300,443 filed Jun. 26, 2001, and the benefit of priority of U.S. provisional patent application No. 60/304,402 filed Jul. 12, 2001.

FIELD AND BACKGROUND OF THE INVENTION

The present invention relates to methods of preventing or reducing pathogenesis of oxidant stress-associated diseases of the aerodigestive tract. More particularly, the present invention relates to methods of employing hydroxocobalamin (vitamin B12a, OH—CO), deferoxamine (DES) and reduced glutathione (GSH) to reduce or prevent tobacco smoke (TS)-induced cellular or macromolecular damage in the aerodigestive tract.

Harmful Effects of Tobacco Consumption:

The deleterious effects of tobacco abuse, principally via cigarette smoking, are well known. Tobacco is a worldwide public health hazard accounting for significant morbidity and mortality. Although smoking places an abundant oxidant insult to the oropharynx and respiratory tract, the oxidant burden is deleterious to the entire body of the tobacco consumer. Namely, tobacco consumption leads to development or enhancement of atherosclerosis, cardiovascular disease, chronic obstructive pulmonary disease and various forms of cancer, including carcinomas of the mouth, pharynx, esophagus and lung.

There are three principal ways to consume tobacco: smoking, chewing and dipping and snuffing. Approximately 50 million Americans smoke and countless others are affected by tobacco smoke (TS) as secondary smokers. Children of smokers breathe this second-hand smoke and have more respiratory problems than children of non-smokers. Smokeless tobacco is used by as many as 12 million individuals and has a detrimental effect on the oral cavity plus systemic effects from buccal absorption of nicotine and other chemicals. Chewing looseleaf tobacco and "dipping" moist, ground snuff tobacco are common uses of tobacco without smoking.

Studies have estimated that TS has over 3,000 different constituents, of which many are toxic, carcinogenic and/or generate free radical species. Free radicals are atoms or molecules containing an unpaired electron. Oxygen free radicals include the superoxide free radical ($.O_2^-$) and the hydroxyl radical (OH.) which, together with hydrogen peroxide ($H_2O_2$) and singlet oxygen ($^1O_2$), are jointly called reactive oxygen species (ROS). Due to their high reactivity they may lead to chemical modification and impairment of the components of living cells, such as proteins, lipids, carbohydrates and nucleotides.

Tobacco smoke mediated oxidant injury is similar to that induced by smog, thereby increasing such noxious stimuli to primary and secondary smokers in polluted atmospheric environments.

Most of constituents of TS have been identified in so-called mainstream and side stream TS. The former is that volume of smoke drawn through the mouthpiece of the tobacco product during puffing while side stream smoke is that smoke emitted from the smoldering cigarette in between puffs. Although tar and nicotine are retained in the filter of cigarettes, this applies mainly to mainstream smoke, when comparing filter and non-filter cigarettes. Mainstream smoke emission is also markedly reduced both in low and in ultra low tar yield cigarettes. However, the emissions of toxic and carcinogenic components in side stream smoke are not significantly reduced in filter cigarettes when compared to non-filter counterparts. Thus, side stream smoke is a major contributor to environmental smoke, affecting both the smoker and their non-smoking counterparts, so called secondary smokers.

Evidence shows that cigars as well as cigarettes are highly toxic and addictive. Tobacco smokers have a similar increased risk for oral and laryngeal cancers. Evidence indicates that one cigar generates levels of carcinogenic particles exceeding those generated by three cigarettes. Fumes from cigars are also of greater consequence to secondary smokers. Epidemiologic studies reveal greater frequencies of heart disease, emphysema, and cancers of the mouth and pharynx in cigar smokers when compared to matched non-smokers. Cigar smokers may spend one full hour smoking a single large cigar and commonly hold an unlit cigar in the mouth, allowing further exposure to toxins by local absorption. Thus, consumption of cigars may produce an equal or greater burden of toxic exposure to TS than cigarettes. Recently, sales of cigars have risen, partly due to their gaining popularity with women and the advent of the female friendly "cigar bar".

Oral Diseases Associated With Tobacco Consumption:

Tobacco, whether smoked or chewed, causes common untoward effects in the oral cavity. Tobacco smoke has two chances to exert its deleterious effects in the mouth; when it is inhaled by the smoker and on its exit during exhalation.

Over 30,000 new cases of cancer of the oral cavity are diagnosed annually, accounting for 2–4 percent of all new cancers. Oral cancer kills 8,000 patients each year and only half of cases diagnosed annually have a five-year survival. The great majority of these patients are users of tobacco products. Oral squamous cell carcinoma (SCC) is the most common malignancy of the head and neck with a worldwide incidence of over 300,000 new cases annually. The disease is characterized by a high rate of morbidity and mortality (approximately 50%) and in this respect is similar to malignant melanoma (1–4). The major inducer of oral SCC is exposure to tobacco which is considered to be responsible for 50–90% of cases world-wide (5, 6). As such, the incidence of oral SCC in tobacco smokers is 4–7 times higher than in non-smokers (7, 8). Moreover, the higher TS-related risk for oral SCC is manifested by a reduction in the mean age of development of the disease by 15 years as compared to non-smokers (9).

Leukoplakia, a tobacco induced white patch on the buccal mucosa, as found in smokers, is a localized irritation due to direct contact of smoked or smokeless tobacco and it is directly related to the frequency and years of tobacco abuse. Although leukoplakia is a benign oral lesion, it has a malignant potential.

In addition, tobacco contributes to other oral symptoms or pathologies of the mouth and teeth. Tobacco may cause halitosis, may numb the taste buds, and interfere with the smell and the taste of food. It may stain teeth and contribute to dental caries. Smokers have more dental tartar (calculus) than non-smokers. Tobacco is associated also with destructive periodontal (gum) disease and tooth loss. Acute necrotizing ulcerative gingivitis ("trench mouth") is a destructive, painful inflammatory condition occurring mainly in tobacco smokers. Swelling of the nasal and sinus membranes have also been associated, purportedly, in individuals who are "allergic" to TS.

Oral submucous fibrosis occurs mainly in India and is a chronic, progressive premalignant condition. The etiology is chronic chewing of tobacco or areca nut or both. The fibrosis results in restriction of mouth opening and involves the palates, tonsillar fossa, buccal mucosa and underlying muscle. Associated with this condition is also oropharyngeal carcinomas, also with a high frequency in India and associated in 70% of cases with chewing tobacco. Smokeless tobacco and areca nut usage is also common in Pakistan, Bangladesh and Java and in these and Indian immigrants to the United States and United Kingdom.

Tobacco smoke also affects the skin adversely. Dr. Douglas Model of England in 1985 added to the medical lexicon the term "smoker's face" from a study with pictures of 116 cases and suitable non-smoking controls (10). Akin to photodamage, those with smoker's face appear older and have more wrinkles.

Molecular Damage Resulting From Exposure to TS: Tobacco smoke induces oxidative damage to lipids, DNA and proteins, particularly via protein-SH groups as a consequence of containing high levels of both free radicals as well as aldehydes, including acetaldehyde (ethanol), propanol and acrolein, as well as other deleterious molecules.

Oxidant Injury: Tobacco smoke is divided into two phases; tar and gas-phase smoke. Tar contains high concentrations of free radicals. Many tar extracts and oxidants are water-soluble and reduce oxygen to superoxide radical which can dismutate to form the potent oxidant $H_2O_2$. Oxidants in gas-phase smoke are reactive carbon- and oxygen-centered radicals with extremely short half lives.

Cells subjected to oxidative stress develop severely affected cellular function and suffer damage to membrane lipids, to proteins, to cytoskeletal structures and to DNA. Free radical damage to DNA has been measured as formation of single-strand breaks, double-strand breaks and chromosomal aberrations. Cells exposed to ionizing radiation and TS have also been demonstrated to have an increased intracellular DNA damage, a precursor of mutations and development of malignancies. It has been shown that TS elicits protein carbonylation in plasma and that, in contrast, exposure of human plasma to gas-phase but not to whole TS produces oxidative damage to lipids.

Redox-Active Metals: Redox-active metal ions, such as iron and copper, in the presence of $H_2O_2$ and other low-reactive free radicals found in TS, such as superoxide radicals, participate in the deleterious Haber-Weiss and Fenton reactions, in which the highly reactive hydroxyl free radicals are produced.

Aldehydes: Studies have shown that exposure of plasma to TS results in protein damage in the form of protein carbonylation (11) and in oxidation of plasma lipids and antioxidants (12). The source of the accumulation of protein carbonylation was found to be due to aldehydes present in TS (13, 14). In addition, it was shown that several salivary enzymes such as amylase, lactic dehydrogenase (LDH), and acid phosphatase were considerably affected by TS (14, 15), where both TS-based aldehydes, such as acrolein and crotonaldehyde, as well as oxygen free radicals were implicated as the causative agents affecting the above enzymes (14, 15).

Physiological Antioxidants:

Glutathione: Glutathione, a sulfur-containing tripeptide (L-γ-glutamyl-1-cysteine-glycine) is the most abundant non-protein thiol in mammalian cells and is recognized as the primordial antioxidant. Glutathione, in its reduced form, "GSH", acts as a substrate for glutathione-S-transferase and glutathione peroxidase, enzymes catalyzing reactions involved in detoxification of xenobiotic compounds and in antioxidation of ROS and other free radicals. This ubiquitous protein plays a vital function in maintaining the integrity of free radical sensitive cellular components. Under states of GSH depletion, including malnutrition and severe oxidative stress, cells may then become injured from excess free radical damage and die.

Oral Peroxidase: Oral peroxidation is the pivotal enzymatic activity of the salivary antioxidant system (16–19). Oral peroxidase activity is composed of the combined activity of two peroxidases, salivary peroxidase (SPO) and myeloperoxidase (MPO). Salivary peroxidase, which is secreted by the major salivary glands, mainly the parotid gland (18), contributes 80% of the total oral peroxidase (OPO) activity, while MPO, produced by leukocytes (20), contributes the remaining 20% of OPO activity. Oral peroxidase performs two functions preventing oxidant injury; it reduces the level of $H_2O_2$ excreted into the oral cavity from the salivary glands, by bacteria and by leukocytes, and it inhibits the metabolism and proliferation of various bacteria in the oral cavity.

Oral peroxidase is involved in destroying TS-associated $H_2O_2$. Tobacco smoke-associated hydrocyanic acid (HCN) is metabolized by the liver to thiocyanate ion ($SCN^-$). This $SCN^-$ is specifically sequestered from the plasma by the parotid gland and is secreted by this gland into the oral cavity. Its concentration in the saliva of non-smokers ranges from 0.3–1.5 mM, while the respective range in smokers is approximately 1.4–4.0 mM, depending on the number of cigarettes smoked per day, with a prolonged $t_{1/2}$ of 9.5 h (21). Following its secretion in saliva, $SCN^-$ reacts with, and eliminates $H_2O_2$ in the oral cavity in a reaction catalyzed by OPO, as described in FIG. 2a. However, it has been shown that if OPO is damaged or depleted, as occurs upon exposure to TS, the $H_2O_2$ in the oral cavity is not eliminated and remains available for further reaction with redox-active metal ions which are secreted via the parotid gland saliva (22, 23).

In the reaction of $SCN^- + H_2O_2 \rightarrow OSCN^- + H_2O$, which is catalyzed by OPO, $H_2O_2$ oxidizes $SCN^-$, a detoxification product of cyanide secreted mainly by the parotid gland. In this reaction, $SCN^-$ acts as the electron-donating component, similarly to GSH in other biological systems (20, 24, 25). Two potent antibacterial oxidizing products evolve from this reaction: hydrogen hypothiocyanite (HOSCN) and its conjugated anion, $OSCN^-$. The antibacterial activity of HOSCN and $OSCN^-$ stems from their ability to react with sulfhydryl groups of bacterial enzymes that are vital for glycolysis, such as hexokinase, aldolase and pyruvate kinase (20, 25–28).

The importance of OPO in oral disease prevention has been demonstrated in several studies. For example, studies using animal models or the Ames test have shown that saliva inhibits the mutagenicity of known oral cancer inducers, such as TS, 4NQO and benzopyrene (29, 30). Biochemical studies have also demonstrated that saliva inhibits production of ROS such as superoxide free radical and $H_2O_2$ from betel quid tobacco, the most potent inducer of oral cancer (31). These observations are further supported in the observation that patients with oral lichen planus, a premalignant lesion, have reduced salivary antioxidant capacity (32).

Several prior art approaches have been employed in order to reduce or prevent incidence of oral disease resulting from oxidant injury.

For example, cigarette filters are used to trap TS tar but do not the gas-phase compounds.

One approach has employed a filter for TS providing chemo-sorptive properties to reduce aldehyde concentration in TS (33).

Another approach has employed oral megadoses of antioxidants in attempts to reduce generation of $H_2O_2$ resulting from the "respiratory burst" reaction associated with phagocytic activity of macrophages and neutrophils. It has been shown that smokers have a higher "respiratory burst" reaction than non-smokers and that this may be associated with the increased incidence of aerodigestive tract disease in the former.

In yet another approach, dipeptide compounds with pharmaceutical properties to increase glutathione levels were employed (34).

A further approach utilized a glycine carboxylic acid alkyl mono-ester of glutathione to increase cellular GSH levels (35).

In yet a further approach, administration of a combination of glutathione and selenium was suggested for preventing oxidant injury resulting from exposure to TS (36).

In another approach, administration of a combination of glutathione, ascorbic acid, selenium and a sulfur-containing amino acid was suggested in order to prevent oral oxidant injury (37).

In yet another approach, administration of a combination including some or all of the following antioxidants; L-glutathione, L-selenomethionine, L-selenocysteine, ascorbyl palmitate, ascorbic acid esters, L-cysteine, N-acetyl-l-cysteine, tocopherol acetate, tocopherol succinate, vitamin A, a zinc salt, methionine and taurine was suggested in order to provide intra-oral protection from oxidant injury (38).

All of the aforementioned approaches, however, failed to demonstrate prevention or reduction of loss of OPO activity or $HCN^-$-, redox-active metal ion- or aldehyde-induced cell death or protein carbonylation resulting from TS-associated oxidative stress, processes being further described in the Examples section below.

There is thus a widely recognized need for, and it would be highly advantageous to have, methods of preventing or reducing TS-associated oxidant injury in the aerodigestive tract devoid of the above limitation.

SUMMARY OF THE INVENTION

According to the present invention there is provided a pharmaceutical composition for preventing or reducing tobacco smoke-associated injury in the aerodigestive tract of a subject, the pharmaceutical composition comprises, as an active ingredient, a therapeutically effective amount of an agent capable of preventing or reducing tobacco smoke-associated decrease in peroxidase activity in the aerodigestive tract of the subject, and a pharmaceutically acceptable carrier.

According to further features in preferred embodiments of the invention described below, the agent comprises a cyanide chelator.

According to still further features in the described preferred embodiments, the agent is hydroxocobalamin.

According to still further features in the described preferred embodiments, the pharmaceutically acceptable carrier is selected so as to enable administration of the pharmaceutical composition by a route selected from the group consisting of the intranasal, transdermal, intradermal, oral, buccal, parenteral, topical, rectal and inhalation route.

According to still further features in the described preferred embodiments, the the pharmaceutical composition is formulated as a solution, suspension, emulsion or gel.

According to still further features in the described preferred embodiments, the pharmaceutical composition further includes a formulating agent selected from the group consisting of a suspending agent, a stabilizing agent and a dispersing agent.

According to another aspect of the present invention there is provided a pharmaceutical composition for preventing or reducing tobacco smoke-associated injury in the digestive tract of a subject, the pharmaceutical composition comprises, as an active ingredient, a therapeutically effective amount of an agent capable of preventing or reducing tobacco smoke-associated death of cells in the digestive tract of the subject, and a pharmaceutically acceptable carrier.

According to further features in preferred embodiments of the invention described below, the cells are lymphocytes.

According to still further features in the described preferred embodiments, the agent comprises an iron chelator.

According to still further features in the described preferred embodiments, the agent is deferoxamine.

According to still further features in the described preferred embodiments, the pharmaceutically acceptable carrier is selected so as to enable administration of the pharmaceutical composition by a route selected from the group consisting of the intranasal, transdermal, intradermal, oral, buccal, parenteral, topical, rectal and inhalation route.

According to still further features in the described preferred embodiments, the the pharmaceutical composition is formulated as a solution, suspension, emulsion or gel.

According to still further features in the described preferred embodiments, the pharmaceutical composition further includes a formulating agent selected from the group consisting of a suspending agent, a stabilizing agent and a dispersing agent.

According to yet another aspect of the present invention there is provided a pharmaceutical composition for reducing or preventing tobacco smoke-associated injury in the aerodigestive tract of a subject, the pharmaceutical composition comprises, as an active ingredient, a therapeutically effective amount of an agent capable of preventing or reducing tobacco smoke-associated death of cells in the aerodigestive tract of the subject, and a pharmaceutically acceptable carrier.

According to further features in preferred embodiments of the invention described below, the cells are lymphocytes.

According to still further features in the described preferred embodiments, the agent comprises an antioxidant.

According to still further features in the described preferred embodiments, the agent is glutathione.

According to still another aspect of the present invention there is provided an oral composition in the form of a toothpaste, powder, liquid dentifrice, mouthwash, denture cleanser, chewing gum, lozenge, paste, gel or candy comprising, as an active ingredient, an agent capable of reducing or preventing tobacco smoke-associated loss of peroxidase activity in the aerodigestive tract of a subject.

According to still further features in the described preferred embodiments, the oral composition further comprising at least one flavorant selected from the group consisting of wintergreen oil, oregano oil, bay leaf oil, peppermint oil, spearmint oil, clove oil, sage oil, sassafras oil, lemon oil, orange oil, anise oil, benzaldehyde, bitter almond oil, camphor, cedar leaf oil, marjoram oil, citronella oil, lavendar oil, mustard oil, pine oil, pine needle oil, rosemary oil, thyme oil, and cinnamon leaf oil.

According to an additional aspect of the present invention there is provided an oral composition in the form of a toothpaste, powder, liquid dentifrice, mouthwash, denture cleanser, chewing gum, lozenge, paste, gel or candy comprising, as an active ingredient, an agent capable of reducing or preventing tobacco smoke-associated death of cells in the digestive tract of a subject.

According to yet an additional aspect of the present invention there is provided an oral composition in the form of a toothpaste, powder, liquid dentifrice, mouthwash, denture cleanser, chewing gum, lozenge, paste, gel or candy comprising, as an active ingredient, an agent capable of reducing or preventing tobacco smoke-associated death of cells in the aerodigestive tract of a subject.

According to still an additional aspect of the present invention there is provided a filter comprising an agent being capable of reducing or preventing tobacco smoke-associated loss of peroxidase activity in the aerodigestive tract of a subject, the filter being designed and configured so as to enable release of said agent therefrom when in use by the subject.

According to further features in preferred embodiments of the invention described below, the filter being designed and configured as a tobacco smoke filter.

According to a further aspect of the present invention there is provided a filter comprising an agent being capable of reducing or preventing tobacco smoke-associated death of cells in the digestive tract of a subject, the filter being designed and configured so as to enable release of said agent therefrom when in use by the subject.

According to yet a further aspect of the present invention there is provided a filter comprising an agent being capable of reducing or preventing tobacco smoke-associated death of cells in the aerodigestive tract of a subject, the filter being designed and configured so as to enable release of said agent therefrom when in use by the subject.

According to still a further aspect of the present invention there is provided a filter comprising an agent being capable of reducing or preventing tobacco smoke-associated loss of peroxidase activity in the aerodigestive tract of a subject, the filter being designed and configured so as to enable physico-chemical interaction between said agent and said tobacco smoke when in use by the subject.

According to the present invention there is provided a filter comprising an agent being capable of reducing or preventing tobacco smoke-associated death of cells in the digestive tract of a subject, the filter being designed and configured so as to enable physico-chemical interaction between said agent and said tobacco smoke when in use by the subject.

According to another aspect of the present invention there is provided a filter comprising an agent being capable of reducing or preventing tobacco smoke-associated death of cells in the aerodigestive tract of a subject, the filter being designed and configured so as to enable physico-chemical interaction between said agent and said tobacco smoke when in use by the subject.

According to yet another aspect of the present invention there is provided method of reducing or preventing a tobacco smoke-associated decrease in peroxidase activity in the aerodigestive tract of a subject, the method comprising administering to the subject hydroxocobalamin, in an amount effective for preventing or reducing the tobacco smoke-associated decrease in peroxidase activity in the aerodigestive tract of the subject.

According to still another aspect of the present invention there is provided a method of reducing or preventing a tobacco smoke-associated death of cells in the digestive tract of a subject, the method comprising administering to the subject deferoxamine, in an amount effective for preventing or reducing the tobacco smoke-associated death of cells in the digestive tract of the subject.

According to further features in preferred embodiments of the invention described below, the administering is effected locally or systemically.

According to still further features in the described preferred embodiments, the administering is effected into the oral cavity.

According to an additional aspect of the present invention there is provided a method of reducing or preventing a tobacco smoke-associated death of cells in the aerodigestive tract of a subject, the method comprising administering to the subject glutathione, in an amount effective for preventing or reducing the tobacco smoke-associated death of cells in the aerodigestive tract of the subject.

According to yet an additional aspect of the present invention there is provided a smoking product comprising an agent being capable of reducing or preventing tobacco smoke-associated loss of peroxidase activity in the aerodigestive tract of a subject, the smoking product being designed and configured so as to enable release of said agent therefrom when in use by the subject.

According to still an additional aspect of the present invention there is provided a smoking product comprising an agent being capable of reducing or preventing tobacco smoke-associated death of cells in the digestive tract of a subject, the smoking product being designed and configured so as to enable release of said agent therefrom when in use by the subject.

According to a further aspect of the present invention there is provided a smoking product comprising an agent being capable of reducing or preventing tobacco smoke-associated death of cells in the aerodigestive tract of a subject, the smoking product being designed and configured so as to enable release of said agent therefrom when in use by the subject.

According to yet a further aspect of the present invention there is provided a smoking product comprising an agent being capable of reducing or preventing tobacco smoke-associated loss of peroxidase activity in the aerodigestive tract of a subject, the smoking product being designed and configured so as to enable physico-chemical interaction between said agent and said tobacco smoke when in use by the subject.

According to still a further aspect of the present invention there is provided a smoking product comprising an agent being capable of reducing or preventing tobacco smoke-associated death of cells in the digestive tract of a subject, the smoking product being designed and configured so as to enable physico-chemical interaction between said agent and said tobacco smoke when in use by the subject.

According to the present invention there is provided a smoking product comprising an agent being capable of reducing or preventing tobacco smoke-associated death of cells in the aerodigestive tract of a subject, the smoking product being designed and configured so as to enable physico-chemical interaction between said agent and said tobacco smoke when in use by the subject.

The present invention successfully addresses the shortcomings of the presently known configurations by providing methods of preventing or reducing tobacco smoke-associated injury in the aerodigestive tract.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

and 1 mM deferoxamine (DES), on survival of lymphocytes incubated in the presence of TS and saliva at 37° C.
Asc: ascorbate.

Figure 20:

FIG. 20 is a photograph of Western immunoblotting analysis depicting the effects of several antioxidants on protein carbonylation levels in lymphocyte treated with TS and saliva. Lane 1: incubation in the presence of TS and saliva, Lane 2: incubation in the presence of TS, saliva and 1 mM NAC, Lane 3: incubation in the presence of TS, saliva and 1 mM ascorbate, Lane 4: incubation in the presence of TS, saliva and 1 mM GSH, Lane 5: incubation in the presence of TS, saliva and 1 mM deferoxamine (DES). Incubations were performed at 37° C. for 20 min.

Figure 21:
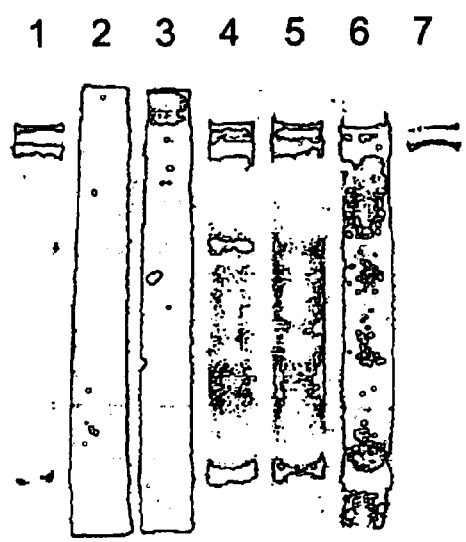

FIG. 21 is a photograph of Western immunoblotting analysis depicting the effects of several volatile aldehydes on lymphocyte carbonylation levels. Lane 1: incubation in the presence of PBS alone, Lane 2: incubation with 80 $\mu$M acrolein, Lane 3: incubation with 20 $\mu$M crotonaldehyde, Lane 4: incubation with 2 $\mu$M acetaldehyde, Lane 5: incubation with 80 $\mu$M acrolein+1 mM GSH, Lane 6: incubation with 20 $\mu$M crotonaldehyde+1 mM GSH, Lane 7: incubation with 2 $\mu$M crotonaldehyde+1 mM GSH. Incubations were performed at 37° C. for 20 min.

Figure 22:
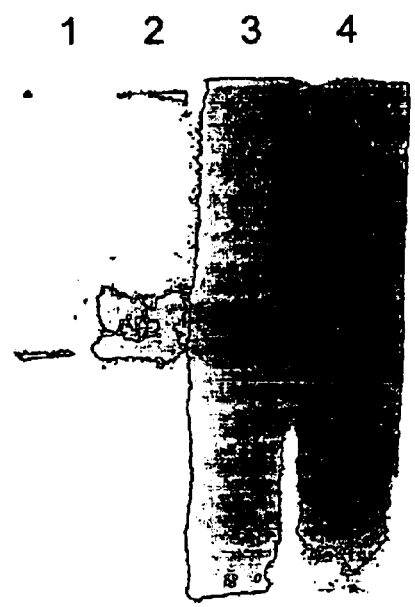

FIG. 22 is a photograph of Western immunoblotting analysis depicting the effects of saliva and acrolein on the lymphocyte protein carbonylation levels. Lane 1: incubation in PBS alone, Lane 2: incubation in the presence of saliva, Lane 3: incubation with 80 $\mu$M acrolein, Lane 4: incubation with 80 $\mu$M acrolein+saliva. Incubations were performed at 37° C. for 20 min.

Figure 23:
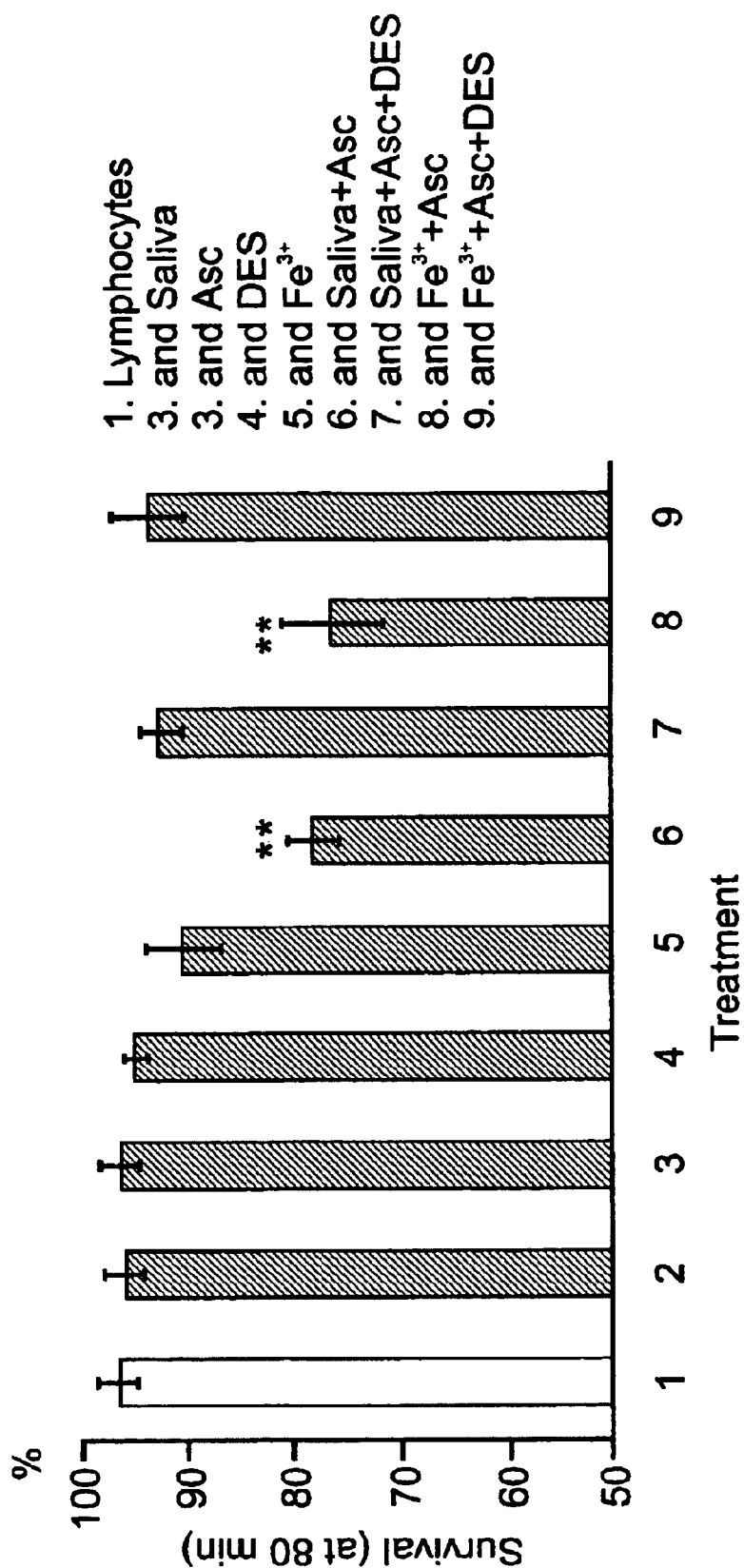

FIG. 23 is a histogram depicting survival of lymphocytes incubated at 37° C. for 20 min in the presence of saliva, various antioxidants and redox-active iron. Column 1: incubation in PBS alone, Column 2: incubation in the presence of saliva, Column 3: incubation in the presence of 1 mM ascorbate, Column 4: incubation in the presence of 1 mM deferoxamine (DES), Column 5: incubation in the presence of 90 $\mu$M FeCl$_3$, Column 6: incubation in the presence of saliva+1 mM ascorbate, Column 7: incubation in the presence of saliva+1 mM ascorbate+1 mM deferoxamine (DES), Column 8: incubation in the presence of 90 $\mu$M FeCl$_3$+1 mM ascorbate, Column 9: incubation in the presence of 90 $\mu$M FeCl$_3$+1 mM ascorbate+1 mM deferoxamine.

Figure 24:
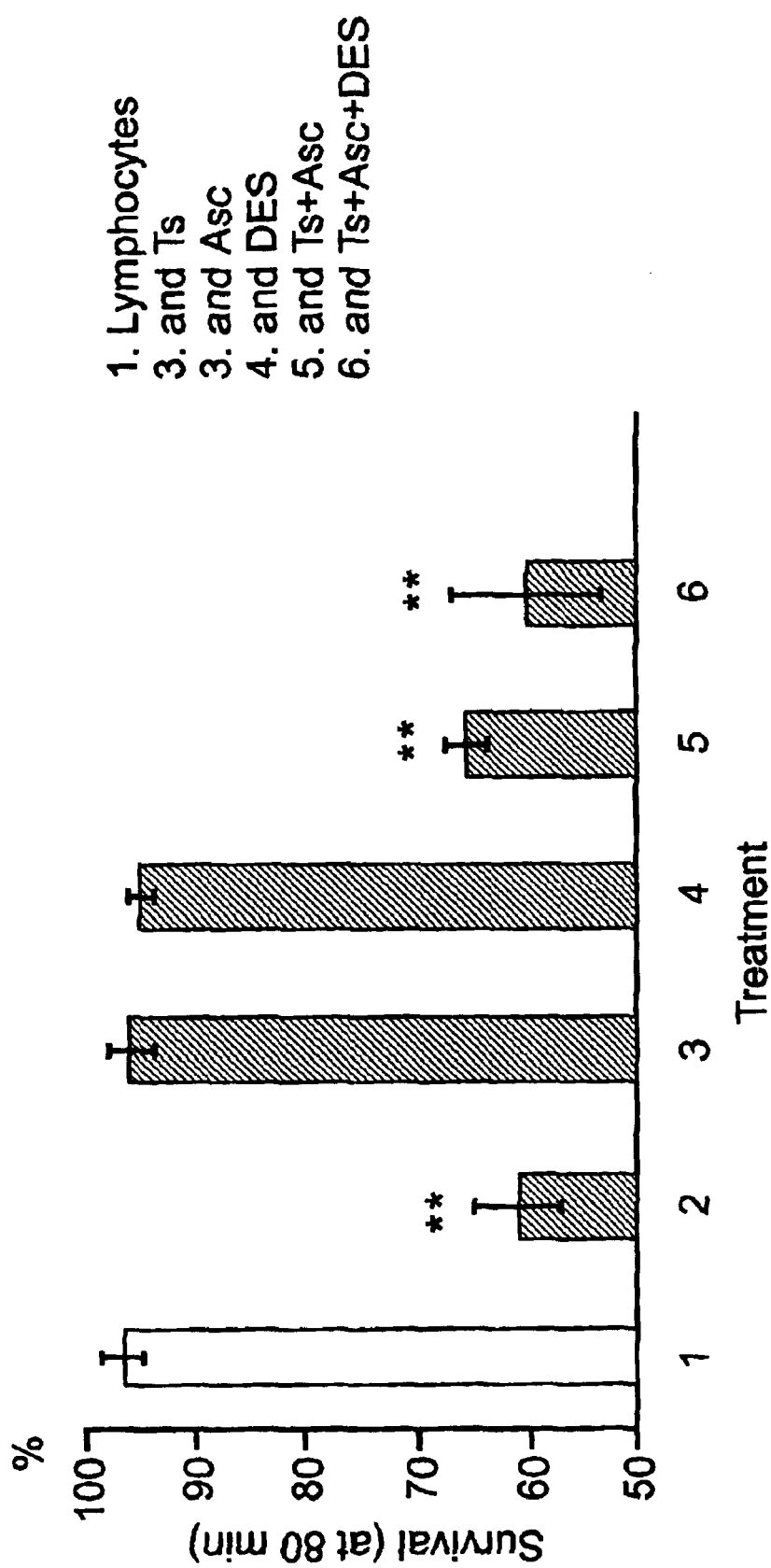

FIG. 24 is a histogram depicting survival of lymphocytes incubated at 37° C. for 80 min in the presence of TS, ascorbate and deferoxamine (DES). Column 1: incubation in PBS alone, Column 2: incubation in the presence of TS, Column 3: incubation in the presence of 1 mM ascorbate, Column 4: incubation in the presence of 1 mM deferoxamine, Column 5: incubation in the presence of TS+1 mM ascorbate, Column 6: incubation in the presence of TS+1 mM ascorbate+1 mM deferoxamine.

Figure 25:
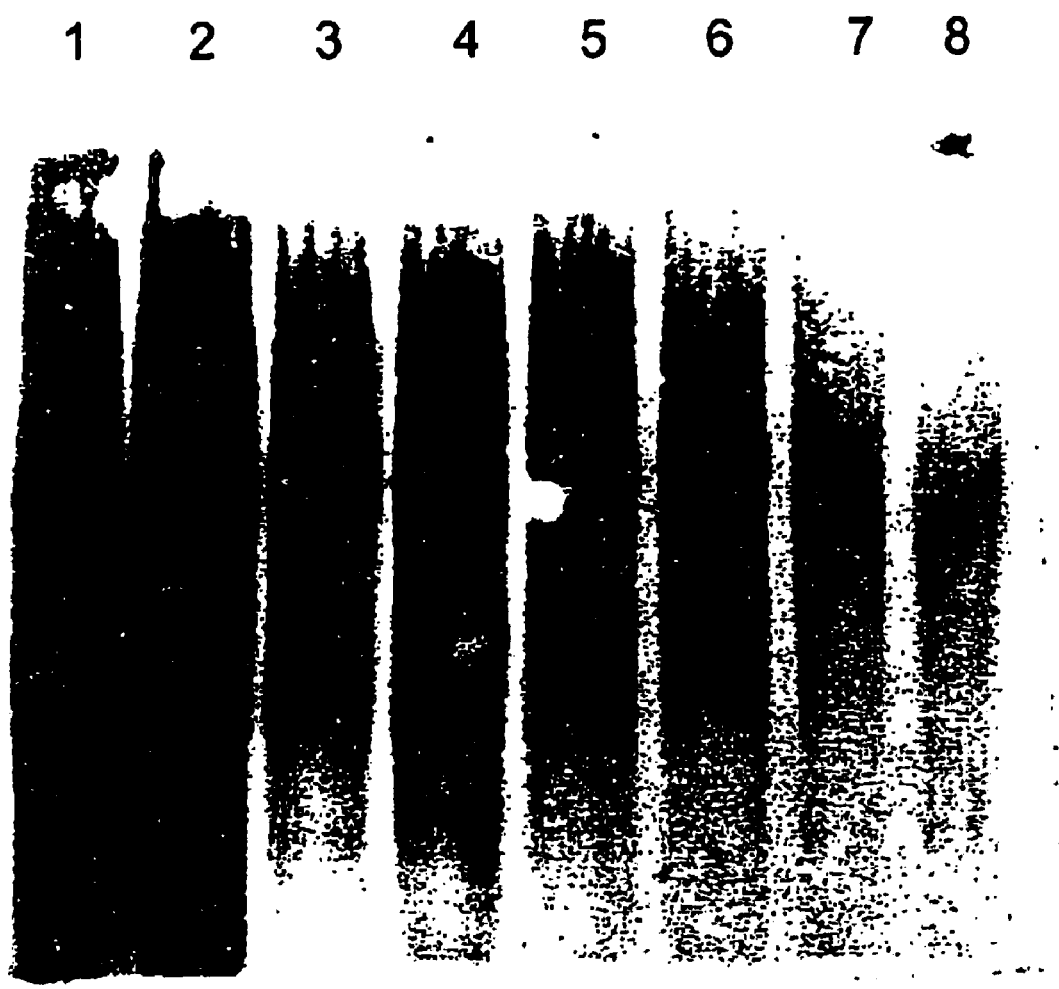

FIG. 25 is a photograph of Western immunoblotting analysis depicting the effects of GSH and deferoxamine (DES) on protein carbonylation levels in lymphocytes incubated for 20 or 80 minutes at 37° C. in the presence of TS and saliva. Lane 1: incubation in the presence of TS+saliva for 20 minutes, Lane 2: incubation in the presence of TS+saliva for 80 minutes, Lane 3: incubation in the presence of TS+saliva+1 mM GSH for 20 minutes, Lane 4: incubation in the presence of TS+saliva+1 mM GSH for 80 minutes, Lane 5: incubation in the presence of TS+saliva+1 mM GSH+1 mM deferoxamine for 20 minutes, Lane 6: incubation in the presence of TS+saliva+1 mM GSH+1 mM deferoxamine for 80 minutes, Lane 7: incubation in the presence of TS+saliva+1 mM GSH+5 mM deferoxamine for 20 minutes, Lane 8: incubation in the presence of TS+saliva+1 mM GSH+5 mM deferoxamine for 80 minutes.

Figure 26:
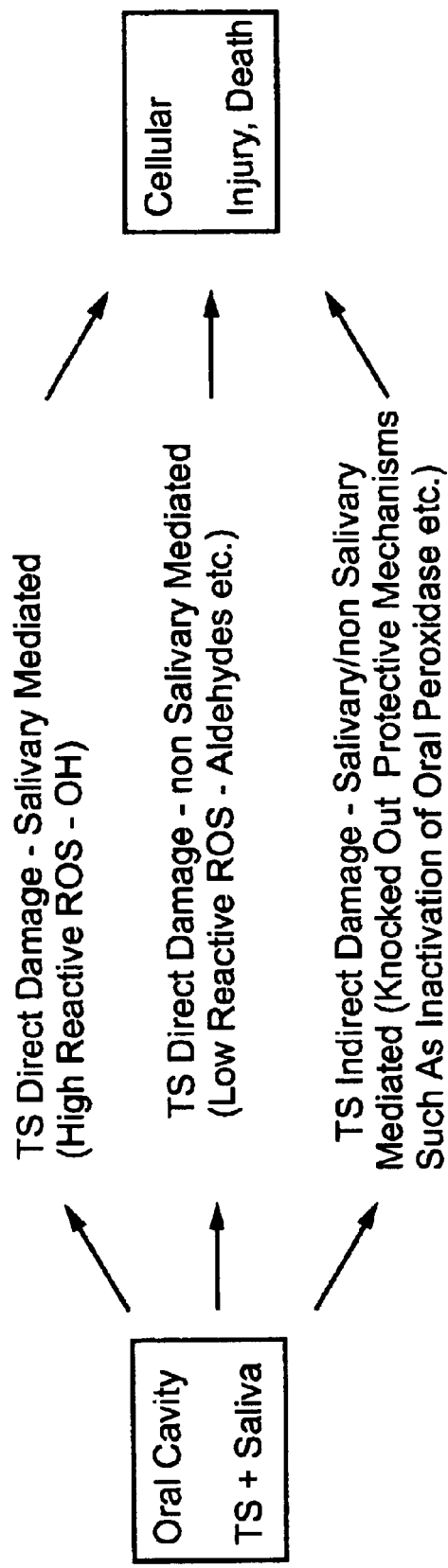

FIG. 26 is a diagram depicting mechanisms of cyanate metabolism following exposure to TS.

DESCRIPTION OF THE PREFERRED EMBODIMENTS

The present invention is of methods, pharmaceutical compositions, oral compositions, filters and tobacco products for preventing or reducing tobacco smoke-associated injury in the aerodigestive tract of a subject. Specifically, the present invention can be used to prevent or reduce loss of OPO activity or CN$^-$-, redox-active metal ion- or aldehyde-induced cell death resulting from TS-associated oxidative stress, all of which being capacities not provided by prior art methods.

The principles and operation of the present invention may be better understood with reference to the drawings and accompanying examples.

Before explaining at least one embodiment of the invention in detail, it is to be understood that the invention is not limited in its application to the details of construction and the arrangement of the components set forth in the following description or exemplified in the Examples. The invention is capable of other embodiments or of being practiced or carried out in various ways. Also, it is to be understood that the phraseology and terminology employed herein is for the purpose of description and should not be regarded as limiting.

Tobacco consumption, such as in the form of smoking, chewing, dipping or snuffing, is associated with pathogenesis of many diseases of the aerodigestive tract.

Thus, various prior art methods of reducing or preventing aerodigestive tract oxidant injury resulting from insults such as TS have been described by the prior art.

For example, various TS filters, including filters for reducing aldehyde concentration in TS have been employed. Administration of various antioxidants, alone or combination with other antioxidants, vitamins, sulfur-containing amino acids or metal co-factors and the like have also been employed. Other approaches have attempted to increase levels of endogenous antioxidants, such as GSH.

While experimenting with approaches for preventing TS-induced oxidant injury in the aerodigestive tract, the present inventors uncovered that exposure to TS leads to decreased OPO activity as well as significant salivary protein carbonylation and that such loss of OPO activity is mediated by CN$^-$ present in TS.

Thus, the present invention provides several approaches which can be used to effectively reduce TS-induced oxidant injury in the aerodigestive tract thus treating diseases caused by tobacco consumption.

As is illustrated in the Examples section which follows, such diseases are characterized by damage to macromolecules, such as, for example, proteins, nucleic acids and lipids. Such damage may take the form of, for example, protein carbonylation, lipid peroxidation and DNA mutations. Such diseases are further characterized by cellular, tissue and organ injury including death of cells such as lymphocytes.

While reducing the present invention to practice the present inventors uncovered that tobacco-related pathologies, and in particular pathologies associated with the aerodigestive tract, can be treated or prevented by various agents.

For example, as is illustrated in Examples 1 of the Examples section which follows, antioxidants such as CN$^-$ chelators can be used to treat TS-associated loss of OPO activity. Examples of CN⁻ chelators, such as OH—CO and additional antioxidants which can be used by this aspect of the present invention are given hereinbelow.

Preferably, the CN⁻ chelator (e.g., OH—CO) is administered in a manner which enables establishment of a concentration of 0.5–2 mM, preferably 1 mM in body fluids, such as saliva.

CN⁻ chelators can be effectively employed to prevent or reduce TS-associated injury in the aerodigestive tract since they act to sequester CN⁻ which is injurious to OPO. Such capacity of OH—CO, also known as the non-CN⁻-bound form of cyanocobalamin, hydroxocobalamin or vitamin B12a, to prevent TS-induced loss of OPO activity represents a marked improvement over prior art methods of preventing TS-mediated oxidant injury of the aerodigestive tract since such protection has never been demonstrated or suggested by prior art methods employing other antioxidants such as GSH, ascorbate or deferoxamine, as shown in Example 1 of the Examples section, below.

As is illustrated in Example 2 of the Examples section which follows, antioxidants functional as redox-active metal ion chelators can be used to treat TS-associated death of cells, such as lymphocytes.

Redox-active metal ion chelators such as deferoxamine, and physiological antioxidants, such as GSH are examples of antioxidants suitable for use by this aspect of the present invention, other examples are given hereinbelow.

Redox-active metal ion chelators are used in a a manner which enables establishment of a 1 mM concentration in body fluids (e.g., saliva). Preferably, deferoxamine is administered in a manner which enables establishment of a concentration of 1 mM, more preferably 5 mM in body fluids. More preferably, a mixture of deferoxamine and GSH is used in a ratio of 1:1, preferably 5:1, respectively. When used in combination, deferoxamine and GSH body fluid concentrations of 1 mM each are desirable although a deferoxamine concentration of 5 mM and a GSH concentration of 1 mM are also therapeutically effective. The use of antioxidants, such as GSH and redox-active metal chelators, such as deferoxamine, preferably in combination, represents a significant improvement over prior art methods of preventing or reducing TS-mediated oxidant injury in the aerodigestive tract.

Examples of CN⁻ chelators suitable for use according to the present invention include, for example, epselen, vitamins A, C and E, selenium compounds, OH—CO, flavenoids, quinones (e.g., Q10, Q9), retinoids and carotenoids.

Examples of redox-active metal ion chelators suitable for use according to the present invention include, for example, epselen, desferioxamine, zinc-desferioxamine, polyamine chelating agents, ethylenediamine, diethylenetriamine, triethylenetetramine, triethylenediamine, tetraethylenepentamine, aminoethylethanolamine, aminoethylpiperazine, pentaethylenehexamine, triethylenetetramine-hydrochloride, tetraethylene-pentamine-hydrochloride, pentaethylenehexamine-hydrochloride, tetraethylpentamine, captopril, penicilamine, N,N'-bis(3-aminopropyl)-1,3-propanediamine, N,N,Bis(2 aminoethyl) 1,3 propane diamine, 1,7-dioxa-4,10-diazacyclododecane, 1,4,8,11-tetraaza cyclotetradecane-5,7-dione, 1,4,7-triazacyclononane trihydrochloride, 1-oxa-4,7,10-triazacyclododecane, 1,4,8,12-tetraaza cyclopentadecane, and 1,4,7,10-tetraaza cyclododecane.

The iron chelator deferoxamine is also known as DES, desferal and desferioxamine.

The various agents described above can be delivered to the affected tissue using one of several modes of administration.

The agents can be administered via a filter which is preferably designed and configured as a TS filter. Such a filter can be incorporated into "filter-tip cigarettes", cigarette holders, gas-masks, protective face-masks, and air-conditioning unit filters.

Figure 1:
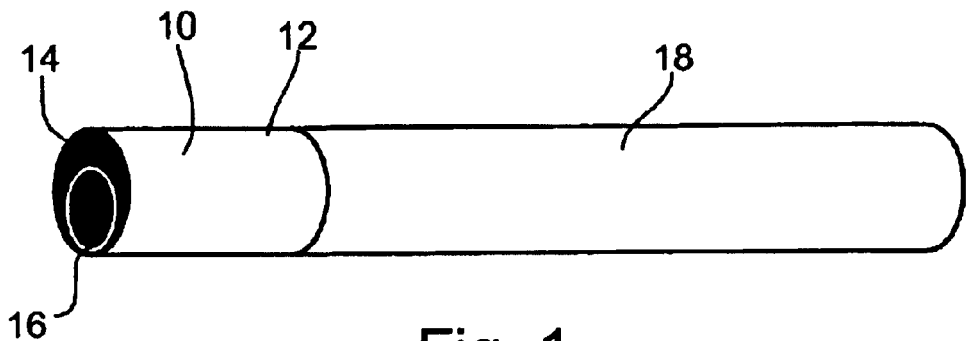
FIG. 1 is schematic diagram depicting the construction of a filter according to the present invention.

FIG. 1 illustrates a cigarrete filter configuration of the TS filter of the present invention which is referred to here-inunder as a cigarette filter 10. Cigarette filter 10 is constructed of a paper lining 12 and a filter core 14 which is composed of glass fiber and is positioned adjacent to a tobacco filling 18. To enable effective delivery the agent of the present invention can be disposed as an aqueous emulsion within a rupturable capsule 16 positioned at the front of filter core 14. Alternatively, the agent may also be dispersed, impregnated in tobacco filling 18 or provided throughout in droplets or beadlets through the employment of gelatin or other colloidal materials, so that the agent can be easily entrained by the smoke passing through filter core 14.

Such filters have been previously described in patent documents (39, 40), the teachings of which are herein incorporated by reference.

Such tobbaco filters can be used as follows. Prior to lighting up, pressure is applied to rupturable capsule 16, so that the released active materials are dispersed within filter core 14, whereby the agent is accessible to the cigarette smoke passing through.

Thus the filter and the smoking product are preferably designed and configured so as to enable physico-chemical interaction between the therapeutic agent and the TS and, more preferably, so as to enable release of the therapeutic agent therefrom when in use by a subject.

According to another preferred embodiment of the present invention the agent or agent combinations described here-inabove are delivered as part of an oral compositions.

Such oral compositions can be in the form of a toothpaste, powder, liquid dentifrice, mouthwash, denture cleanser, chewing gum, lozenge, paste, gel or candy and preferably further comprises at least one flavorant such as wintergreen oil, oregano oil, bay leaf oil, peppermint oil, spearmint oil, clove oil, sage oil, sassafras oil, lemon oil, orange oil, anise oil, benzaldehyde, bitter almond oil, camphor, cedar leaf oil, marjoram oil, citronella oil, lavendar oil, mustard oil, pine oil, pine needle oil, rosemary oil, thyme oil, and cinnamon leaf oil.

Chewing gums for delivery of therapeutic antioxidants have been extensively described in a patent (36) incorporated herein by reference.

The chewing gums, gels or pastes of this invention may include bicarbonates with thickening agents in a concentration from 0.5% to 5.0% by weight. State of the art thickeners with bicarbonate and zinc salts include, but are not limited to chicle, xanthan, arabic, karaya or tragacanth gums. Alginates, carrageenans and cellulose derivatives such as sodium carboxymethyl, methyl, or hydroxy ethyl compounds are appropriate for the intended preparations; surfactants and abrasives may also be included. Alcohols will otherwise be avoided for their known risk factor for oral cancers. In order to decrease dental cavities and add flavor, without using metabolizable sugars, sweetening agents as saccharin, sodium cyclamate, sorbitol, aspartamane and others may be used in concentrations from 0.005% to 5.0% by weight of the total composition, albeit the polyol xylitol, is preferred. Xylitol has been shown to prevent dental caries and decrease gum disease, in part by reducing the putative oral bacteria, especially Streptococcus mutans.

Gels and dentifrices may contain fluoride anticaries compounds. These fluoride compounds, such as salts of sodium, potassium, calcium, magnesium, stannous and others have been known to protect teeth from developing cavities. Fluorides may be present in various amounts in the gels, pastes, gums or lozenges ranging from 0.01% to 3.0% by weight, preferably from 0.05% to 2.0% by weight, most preferably from 0.1% to 1.2% by weight. These sources of stabilized fluoride are taught in a patent which is herein incorporated by reference (41). These compositions should release from 25 to 2000 PPM of the fluoride ion. The aforementioned patent taught a peroxygen compound, a fluoride and a zinc compound to inhibit the decomposition of the former. Thus, fluorides, optionally may be incorporated in the gels or pastes of these antioxidant preparations to prevent and repair free radical-induced gingival diseases.

According to another preferred embodiment of the present invention the agent or agent combinations described hereinabove are delivered as part of a pharmaceutical composition which further includes a pharmaceutically acceptable carrier.

As used herein a "pharmaceutical composition" refers to a preparation of one or more of the compounds described herein, or physiologically acceptable salts or prodrugs thereof, with other chemical components such as pharmaceutically acceptable carriers and excipients. The purpose of a pharmaceutical composition is to facilitate administration of a compound to an organism.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

Pharmaceutical compositions may also include one or more additional active ingredients, such as, but not limited to, anti-inflammatory agents, antimicrobial agents, anesthetics in addition to the antioxidant compounds.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active compounds into preparations which can be used pharmaceutically. Proper formulation is dependent upon the route of administration chosen.

For injection, the compounds of the invention may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient.

Preferably pharmaceutical compositions are formulated as solutions, suspensions, emulsions or gels and may further include a formulating agent such as a suspending agent, a stabilizing agent or a dispersing agent.

Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carbomethylcellulose; and/or physiologically acceptable polymers such as polyvinylpyrrolidone (PVP). If desired, disintegrating agents may be added, such as cross-linked polyvinylpyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For administration by inhalation, the compounds for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

Pharmaceutical compositions for parenteral administration include aqueous solutions of the active preparation in water-soluble form. Additionally, suspensions of the active compounds may be prepared as appropriate oily injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile, pyrogen-free water, before use.

The compounds of the present invention may also be formulated in rectal compositions such as suppositories or retention enemas, using, e.g., conventional suppository bases such as cocoa butter or other glycerides The pharmaceutical compositions herein described may also comprise suitable solid of gel phase carriers or excipients. Examples of such carriers or excipients include, but are not limited to, calcium carbonate, calcium phosphate, various sugars, starches, cellulose derivatives, gelatin and polymers such as polyethylene glycols.

Pharmaceutical compositions suitable for use in context of the present invention include compositions wherein the active ingredients are contained in an amount effective to achieve the intended purpose. More specifically, a therapeutically effective amount means an amount of antioxidant preparation effective to prevent, alleviate or ameliorate symptoms of disease or prolong the survival of the subject being treated.

Determination of a therapeutically effective amount is well within the capability of those skilled in the art, especially in light of the detailed disclosure provided herein.

Toxicity and therapeutic efficacy of the compounds described herein can be determined by standard pharmaceutical procedures in cell cultures or experimental animals, e.g., by determining the $IC_{50}$ and the $LD_{50}$ (lethal dose causing death in 50% of the tested animals) for a subject compound. The data obtained from these cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition.

Depending on the severity and responsiveness of the condition to be treated, dosing can also be a single administration of a slow release composition, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Examples of injuries to the aerodigestive tract associated with TS include, diseases such as atherosclerosis, cardiovascular disease, chronic obstructive pulmonary disease, various forms of cancer, including malignancies of the mouth, such as oral SCC, malignancies of the pharynx, esophagus and lung, gingival diseases, such as periodontitis and gingivitis and oral diseases, such as leukoplakia, oral submucous fibrosis and conditions such as halitosis.

As used herein, "aerodigestive tract" refers to saliva-lined tissues such as the lips, mouth, buccal cavity, tongue, oropharynx, throat, larynx, esophagus, upper digestive tract, saliva glands, saliva, as well as the similar mucous-lined tissues of the respiratory tract, such as the respiratory mucosa, alveoli, trachea, and lungs.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Example 1

Hydroxocobalamin Provides Protection from Tobacco Smoke-Induced Loss of Aerodigestive Tract Antioxidant Defenses Many common and highly debilitating oral diseases, such as cancer, periodontitis and gingivitis, result from, or are aggravated by consumption of tobacco products, such as tobacco smoking. For example, oral cancer, a frequently lethal and highly debilitating disease, results from tobacco consumption in 50–90% of cases world-wide. One widely accepted mechanism whereby cancer progression is promoted is via oxidant injury, such as protein damage caused by exposure to free radicals.

The present inventors have therefore analyzed the effects of TS on aerodigestive tract antioxidant defenses and have invented means to prevent such effects, as described below.

Figure 2A:
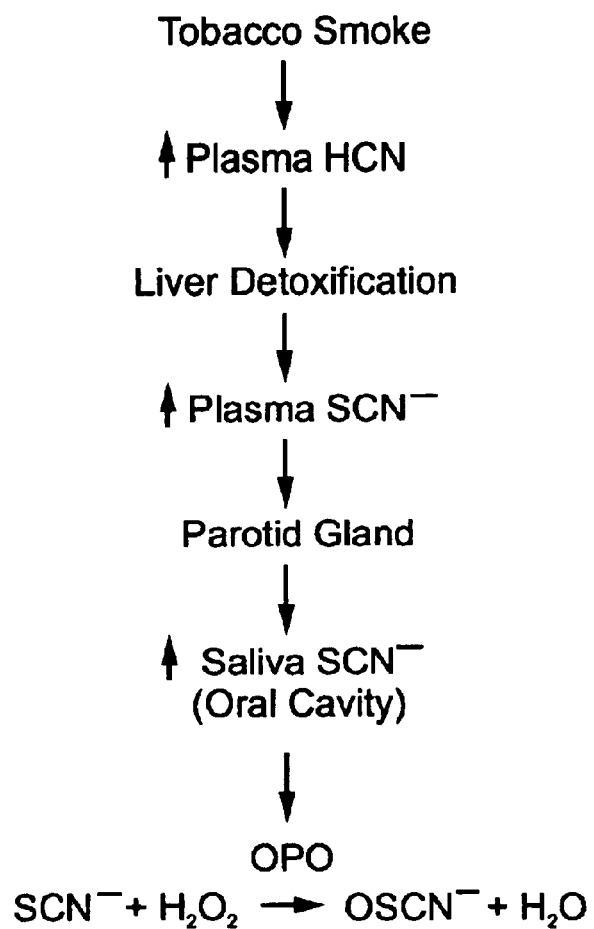
FIG. 2a is a diagram depicting the pathway of cyanate metabolism resulting from exposure to TS-derived HCN.

Exposure to Tobacco Smoke Leads to a Decrease in Oral Peroxidase and to an Increase in Protein Damage:

Oral peroxidase is the critical salivary enzymatic defense against upper digestive tract oxidant injury resulting in, for example, macromolecular damage associated with progression of diseases such as malignancies of the upper digestive tract, periodontitis and gingivitis. The mechanism of OPO mediated protection from antioxidant injury resulting from exposure to TS HCN is schematized in FIG. 2a.

The present inventors, as described below, have therefore analyzed the effects of TS on OPO activity and on salivary protein carbonylation, a well-known indicator of protein damage induced by exposure to oxidative stress and/or TS (11, 12, 42).

Methods and Materials:

Saliva collection: Whole saliva was collected under non-stimulatory conditions from healthy smokers having smoked at least 20 cigarettes a day for at least 10 years and from non-smoking subjects, as previously described (43).

Generation of Tobacco Smoke: Tobacco smoke was obtained from popular commercial cigarettes containing 14 mg of tar and 0.9 mg of nicotine ('Time' cigarettes, Dubek Ltd., Tel Aviv, Israel).

In Vivo Exposure of Saliva to TS: The OPO activity in 2 ml saliva samples of smoker and non-smoker subjects was measured prior to and following the smoking of 1 cigarette. Subjects were prevented from being exposed to TS for 1 h prior to the experiment.

In Vitro Exposure of Saliva to TS: The in vitro exposure of saliva samples to TS was performed using a cigarette combined with a vacuum system, as previously described (11, 12, 14, 15). Briefly, 4–5 ml saliva samples were placed in 50 ml vaccuum flasks with a sidearm to which cigarettes were connected. A vacuum was applied to the flasks and the smoke from 1 cigarette was drawn into the flask in 4–5 "puffs". Saliva samples for analysis of OPO activity were drawn immediately prior to exposure to TS and at 0, 30 and 60 min after completion of exposure of samples to the TS (~10 min). Flasks were incubated in a metabolic shaker at 37° C. Immediately following collection, samples were centrifuged at 800×g for 10 minutes at 4° C. to remove squamous cells and cellular debris. The resulting supernatants were subsequently analyzed for OPO activity and salivary protein carbonylation.

Analysis of OPO Activity: OPO activity was measured according to the 2-nitrobenzoic-thiocyanate (NBS-SCN) assay, as previously described (20). Briefly, DTNB is reduced to NBS by addition of β-mercaptoethanol and decreases in NBS concentration by reaction with OSCN⁻, a product of OPO, are monitored spectrophotometrically by measuring absorbance at 412 nm at pH 5.6 (18). One unit of enzyme activity was defined as the activity required to cleave 1 μmol of NBS/min at 22° C., using a molar extinction coefficient of 12,800 (20).

Western Immunoblotting Analysis of Protein Carbonylation: Salivary proteins were separated by SDS-PAGE using a 10% gel and electro-blotted onto nitrocellulose membranes, as previously described (14). The Oxyblot Kit (Intergen Co, Purchase N.Y.) was used with anti-dinitrophenyhydrazine (DNPH) antibodies to label carbonylated proteins. Protein carbonylation levels were then visualized by reacting labelled blots with a secondary HRP-conjugated anti-rabbit antibody followed by ECL detection of secondarily labelled proteins, as previously described (14).

Statistical Analysis of Results: Ranges, means and SDs and SEMs were computed from the results derived from the smoker and non-smoker experimental subgroups for the in vivo and in vitro studies. Statistical analysis to compare results from subgroups was performed via 2-sample T-test for differences in means using p<0.05 as criteria to establish statistically significant differences.

Results:

Smoking Tobacco Smoke Leads to Impaired Oral Peroxidase Activity In Vivo: Following at least 1 h without exposure to TS, OPO activity levels in saliva samples from smoker subjects were found to be 82% and 85% that of non-smoker subjects in the subjects employed for the in vivo and in vitro studies, respectively, however statistical analysis indicated that these differences were not statistically significant, therefore it was concluded that baseline OPO activity levels were similar in both smokers and non-smokers (Table 1).

TABLE 1

Basal oral peroxidase activity levels in non-smoker and smoker subjects employed for the in vitro and in vivo studies are similar.

|  | In vivo studies (U/ml) | | In vitro studies (U/ml) | |
| --- | --- | --- | --- | --- |
|  | Smokers | Non-smokers | Smokers | Non-smokers |
| N | 17 | 16 | 7 | 11 |
| Range | 180–1,728 | 193–1,019 | 397–1,094 | 236–1,166 |
| Mean | 696 | 573 | 595 | 517 |
| SD | 417 | 252 | 237 | 299 |
| SEM | 101 | 62.9 | 90 | 91 |

Figure 2B:
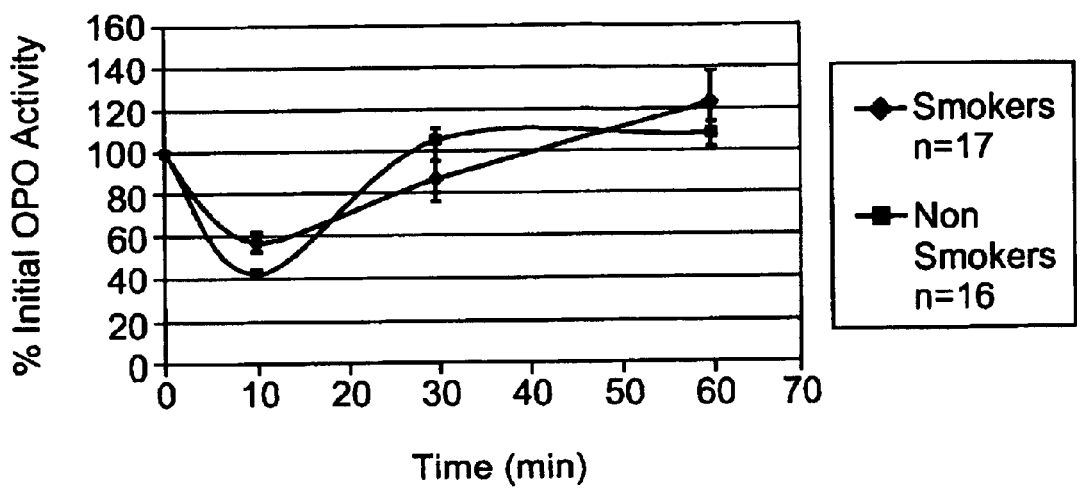
FIG. 2b is a data plot depicting reduced OPO activity following in vivo exposure (smoking) to TS in smoker and non-smoker subjects. The OPO activity of 17 smokers and 16 non-smokers was measured prior to and following smoking 1 cigarette.

Immediately following the smoking of 1 cigarette, a sharp drop in OPO activity levels was observed in both smoker and non-smoker subjects, with levels dropping further in the non-smokers (42.5% of pre-smoking levels, p<0.01) than in the smokers (58.5% of pre-smoking levels, p<0.01) (FIG. 2b). In the absence of subsequent exposure to TS, OPO activity levels returned to 90–100% of initial pre-smoking levels in both groups at 30 min post-smoking.

Figure 2C:
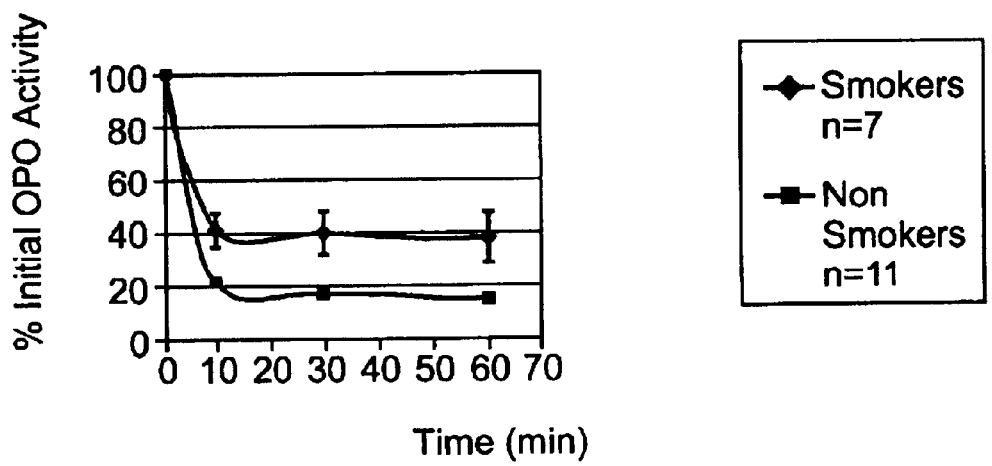
FIG. 2c is a data plot depicting reduced OPO activity following in vitro exposure of saliva to TS in smoker and non-smoker subjects. The OPO activity of 7 smokers and 11 non-smokers was measured prior to and following exposure to 1 cigarette.

In Vitro Exposure to Tobacco Smoke Results in Decreased Oral Peroxidase Activity: A different set of non-smoker and smoker subjects than those employed for the in vivo study were employed for the in vitro study. Similarly to the results obtained in the in vivo experiments described above, OPO activity levels were found to be significantly decreased at Time 0 following exposure to the TS from 1 cigarette in both study groups with loss of OPO activity being more pronounced in non-smoker saliva than in smoker saliva (FIG. 2c).

Figure 3:
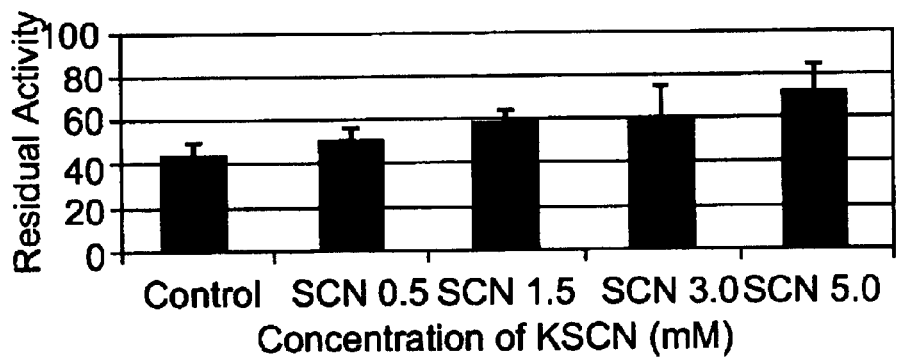
FIG. 3 is a histogram depicting KCSN-mediated resistance to TS exposure-induced decreases in OPO activity in saliva of non-smoker subjects exposed to the TS from 1 cigarette in vitro. Each value represents the average value obtained in experiments on 3 subjects±standard deviation (SD).

The literature reports that the saliva of non-smokers contains 0.3–1.5 mM SCN⁻, while that of heavy smokers contains 1.4–4.0 mM SCN⁻, it was postulated that the higher quantities of SCN⁻ in heavy smokers provide protection against TS-induced reduction in OPO activity. Thus, in order to ascertain why OPO activity was slightly higher and more resistant to TS in smokers relative to non-smokers, the effect of the exogenous addition of SCN⁻ in the form of potassium thiocyanate (KSCN) to non-smoker saliva exposed to TS was analyzed. Addition of 0.5–5.0 mM KSCN to the saliva of 3 non-smoking subjects in the in vitro system and measuring OPO activity before and after smoking 1 cigarette demonstrated that addition of SCN⁻ indeed provides significant protection against loss of OPO activity (FIG. 3).

Figure 4A:
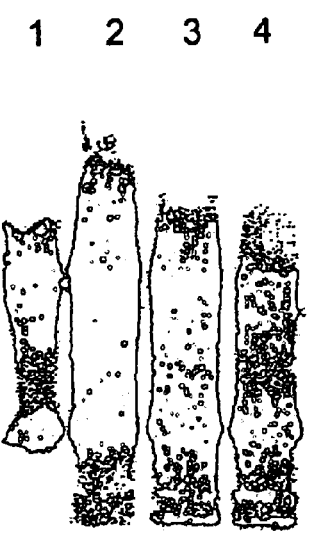
FIGS. 4a–b are photographs of Western immunoblotting analysis depicting increased levels of salivary protein carbonylation in representative non-smoker saliva following in vivo exposure of saliva (smoking) to the TS of 1 cigarette (FIG. 4a). Proof that equal quantities of proteins were analyzed per sample is shown via Coomassie Blue staining (FIG. 4b) of the samples. Abbreviations: amylase (Amy), protein rich proteins (PRP's), lysozyme (Lys). Lane 1: prior to smoking, Lane 2: 10 mins after smoking, Lane 3: 30 mins after smoking, Lane 4: 60 mins after smoking.
Figure 4B:
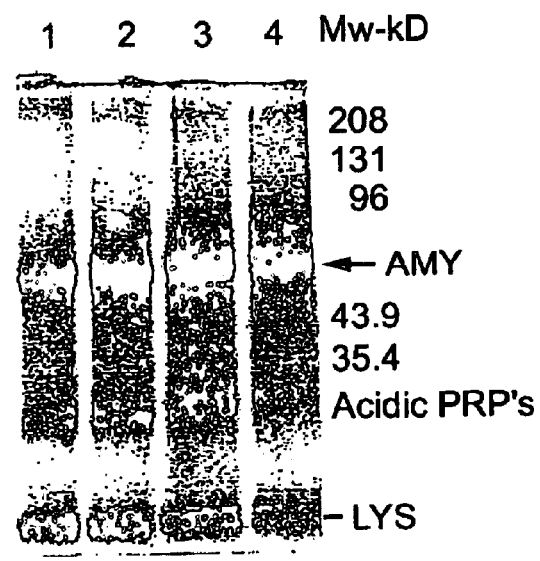

In Vivo Exposure of Saliva to TS Causes Significant Salivary Protein Carbonylation: In vivo exposure of saliva to TS, via smoking of 1 cigarette, was found to cause significant increases in levels of salivary protein carbonylation, as assessed by Western immunoblotting analysis (FIG. 4a). The highest levels of protein carbonylation were observed at 10 min post-smoking (FIG. 4a, Lane 2). The major salivary proteins, such as amylase, acidic proline rich proteins and lysozyme were the ones found to be most carbonylated by TS.

Figure 5A:
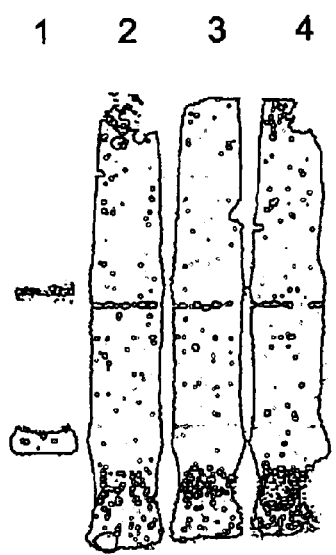
FIGS. 5a–b are photographs of Western immunoblotting analysis depicting increased levels of salivary protein carbonylation in representative non-smoker saliva following in vitro exposure of saliva to the TS of 1 cigarette (FIG. 5a). Proof that equal quantities of proteins were analyzed per sample is shown via Coomassie Blue staining (FIG. 5b) of the samples. Lane 1: prior to exposure to TS, Lane 2: 10 mins following exposure to TS, Lane 3: 30 mins following exposure to TS, Lane 4: 60 mins following exposure to TS.
Figure 5B:
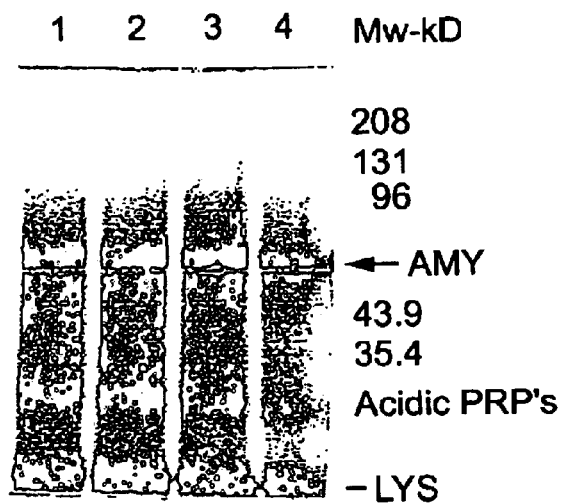

In Vitro Exposure of Saliva to TS Causes Significant Salivary Protein Carbonylation: Similarly to the in vivo studies described above, in vitro exposure of saliva to the TS of 1 cigarette was found to cause significant increases in levels of carbonylation of major salivary protein, as assessed by Western immunoblotting analysis (FIG. 5a). No recovery in the level of protein carbonylation was found in the in vitro studies, as provision of new saliva is not possible.

These results therefore identify loss of OPO activity and concomitant macromolecular damage, such as salivary protein carbonylation, as resulting from exposure to TS.

Hydrocyanic Acid (HCN) Mediates Tobacco Smoke-Associated Loss of Oral Peroxidase Activity:

In order to elucidate the mechanism(s) whereby TS causes loss of OPO activity, the effect of various oxidants and antioxidants on OPO activity in saliva exposed to TS in vitro were analyzed, as described below.

Materials and Methods:

Generation of Tobacco Smoke: Tobacco smoke was obtained from popular commercial cigarettes containing 14 mg of tar and 0.9 mg of nicotine ('Time' cigarettes, Dubek Ltd., Tel Aviv, Israel).

In Vitro Exposure of Saliva to TS: The in vitro exposure of saliva samples to TS was performed as described above with the modification that the same saliva samples were subjected to multiple exposures to the TS of 1 cigarette at 20 min intervals.

Analysis of OPO Activity: Analysis of OPO activity in TS-treated saliva samples was performed as described above.

Treatment of Saliva With TS in the Presence of Oxidants, Antioxidants, and Inhibitors: The various reagents and materials were added to saliva prior to treatment with TS at the specified concentrations. Unless otherwise specified, all chemicals were obtained from Sigma Chemical Corp. (St. Louis, Mo., USA).

Statistical Analysis: Compilation and statistical analysis of results was performed as described above for in vitro studies.

Figure 6:
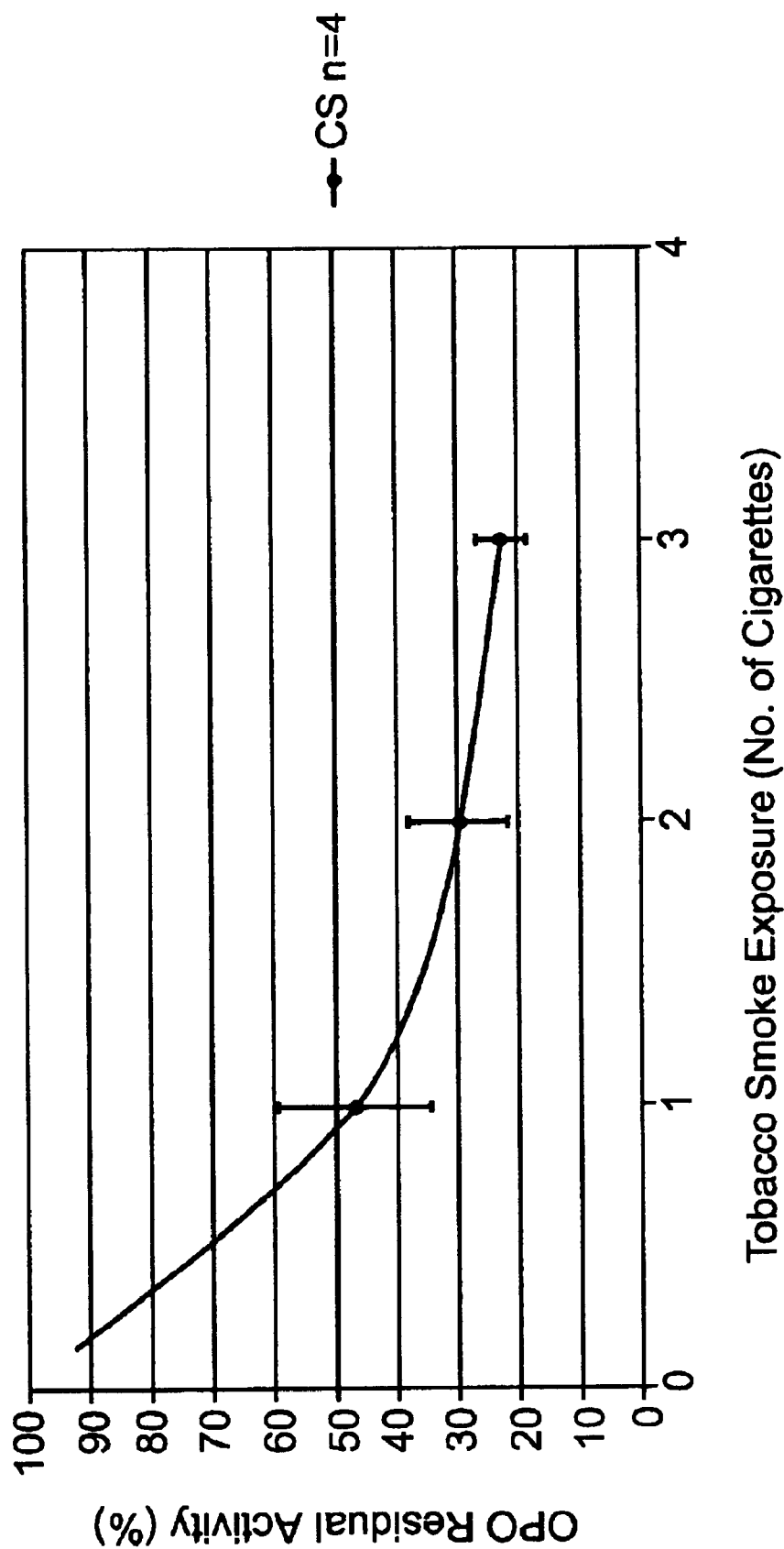
FIG. 6 is a data plot depicting TS dose-dependent decrease in OPO activity in saliva exposed in vitro to 3 exposures of TS over a 1 h period. Each data point represents mean±standard error of the means (SEM) of results from experiments on saliva from 4 subjects.

Results:

Exposure of saliva to the TS of 3 cigarettes resulted in a TS dose-dependent decrease in OPO activity to 22% of pre-TS exposure levels (FIG. 6).

Figure 7:
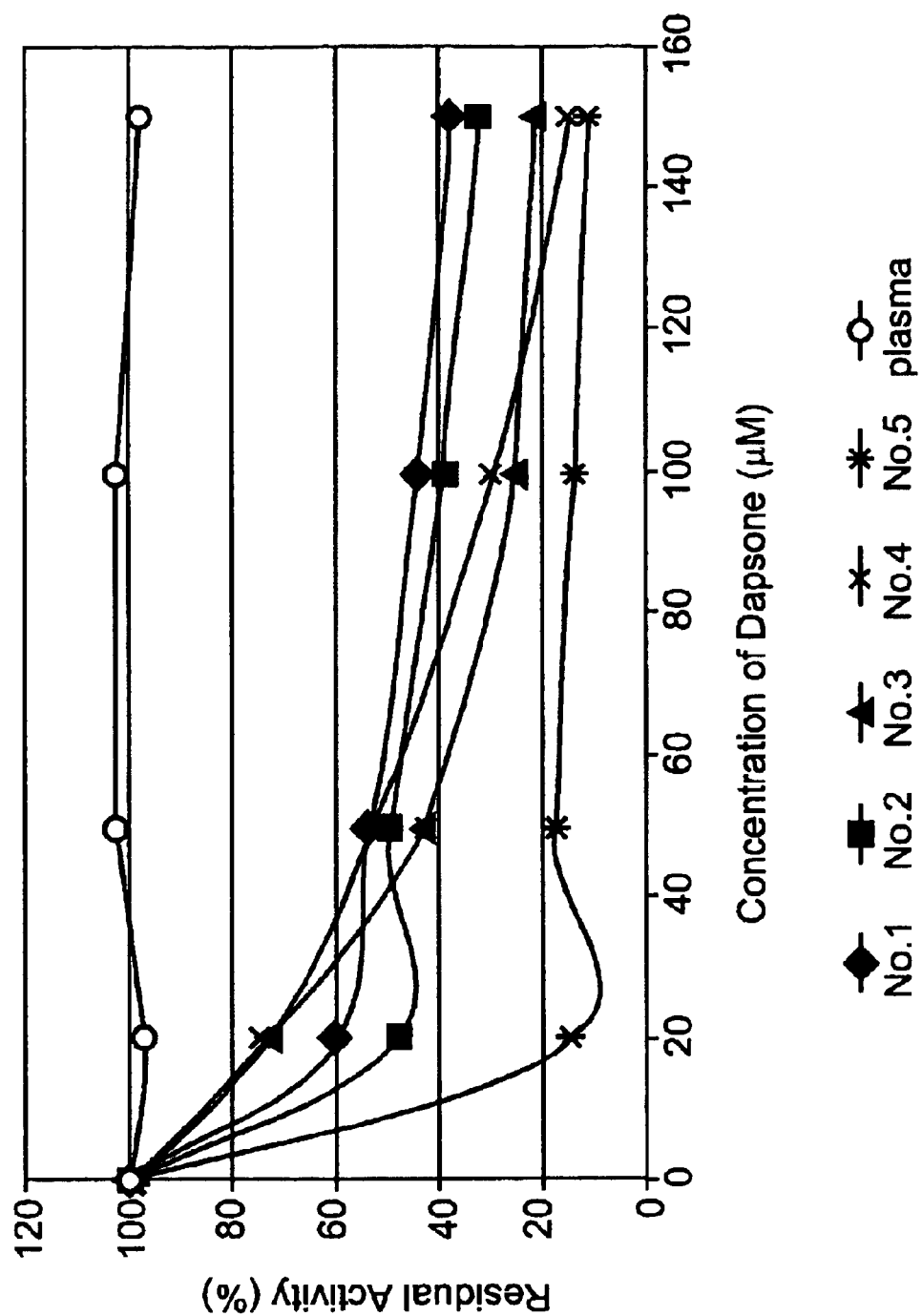
FIG. 7 is a data plot depicting the effect of increasing concentrations of dapsone (4-aminophenylsulfone) on OPO activity in TS-treated saliva. Abbreviations: NO.1, NO.2, NO.3, NO4 and NO.5 correspond to saliva from 5 different subjects and plasma corresponds to commercial MPO.
Figure 8:
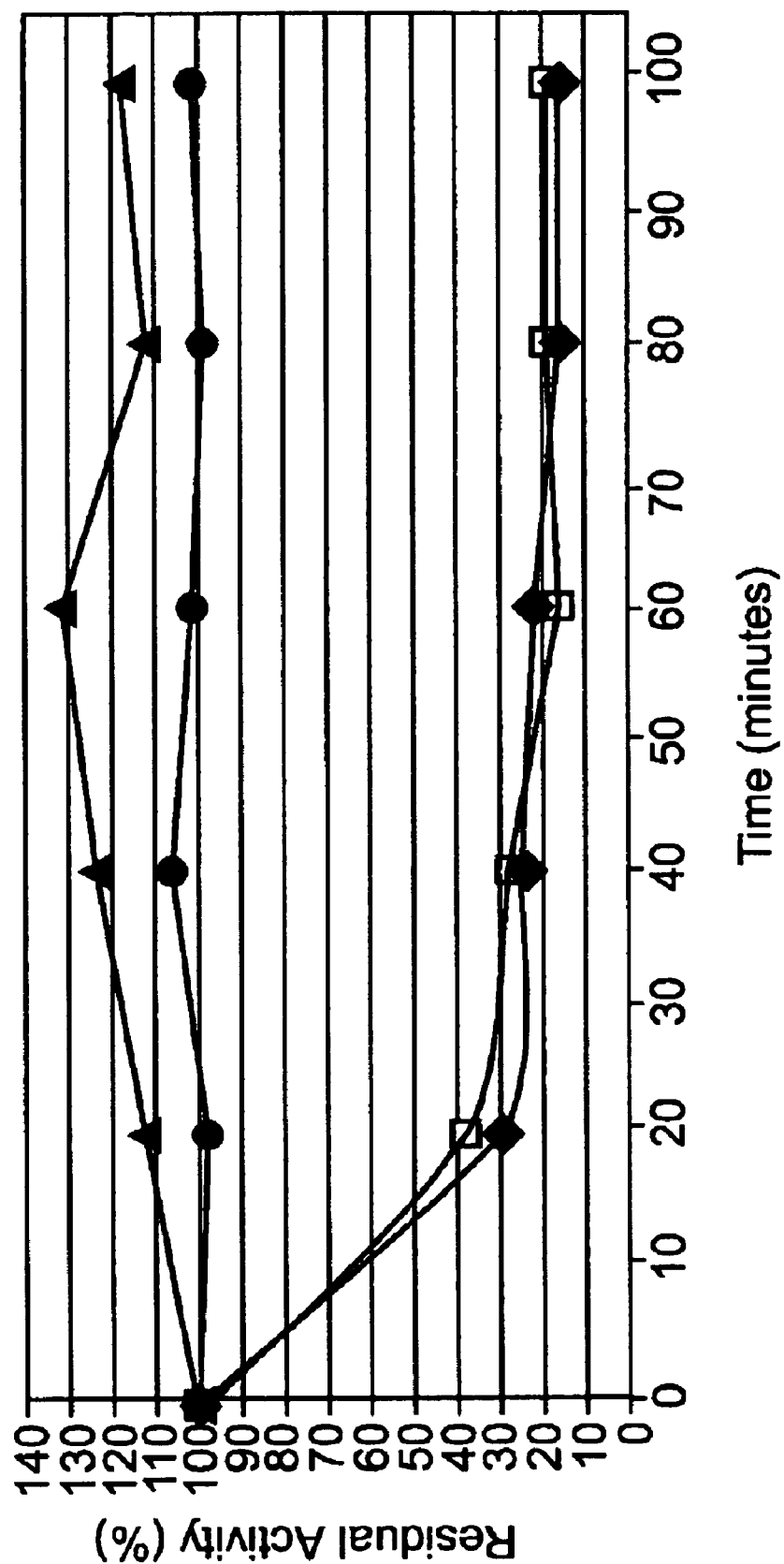
FIG. 8 is a data plot depicting the effect on OPO activity in saliva treated with TS in the presence or absence of 150 $\mu$M dapsone. Saliva samples were normalized with respect to initial OPO activity. OPO exposed to TS in the presence (□) or absence (♦) of dapsone, control saliva exposed to air in the presence (▲) or absence (●) of dapsone.

Dapsone (a gift of J. P. Eiserich), has been shown to specifically inhibit SPO but not MPO at acidic pH (44). Thus, in order to determine which of the MPO or SPO activity components of OPO activity are lost as a result of exposure to TS, OPO activity in TS-treated saliva was measured in the presence of increasing concentrations of 50–150 µM dapsone. Loss of OPO activity due to exposure to TS was found to be 60–85% in the presence of 150 µM of dapsone whereas control MPO activity was unaffected, (FIG. 7) and loss of OPO activity was similar in the presence or absence of 150 µM dapsone in saliva containing ~40% MPO (FIG. 8) indicating that TS affects SPO and MPO activities to a similar extent.

Figure 9:
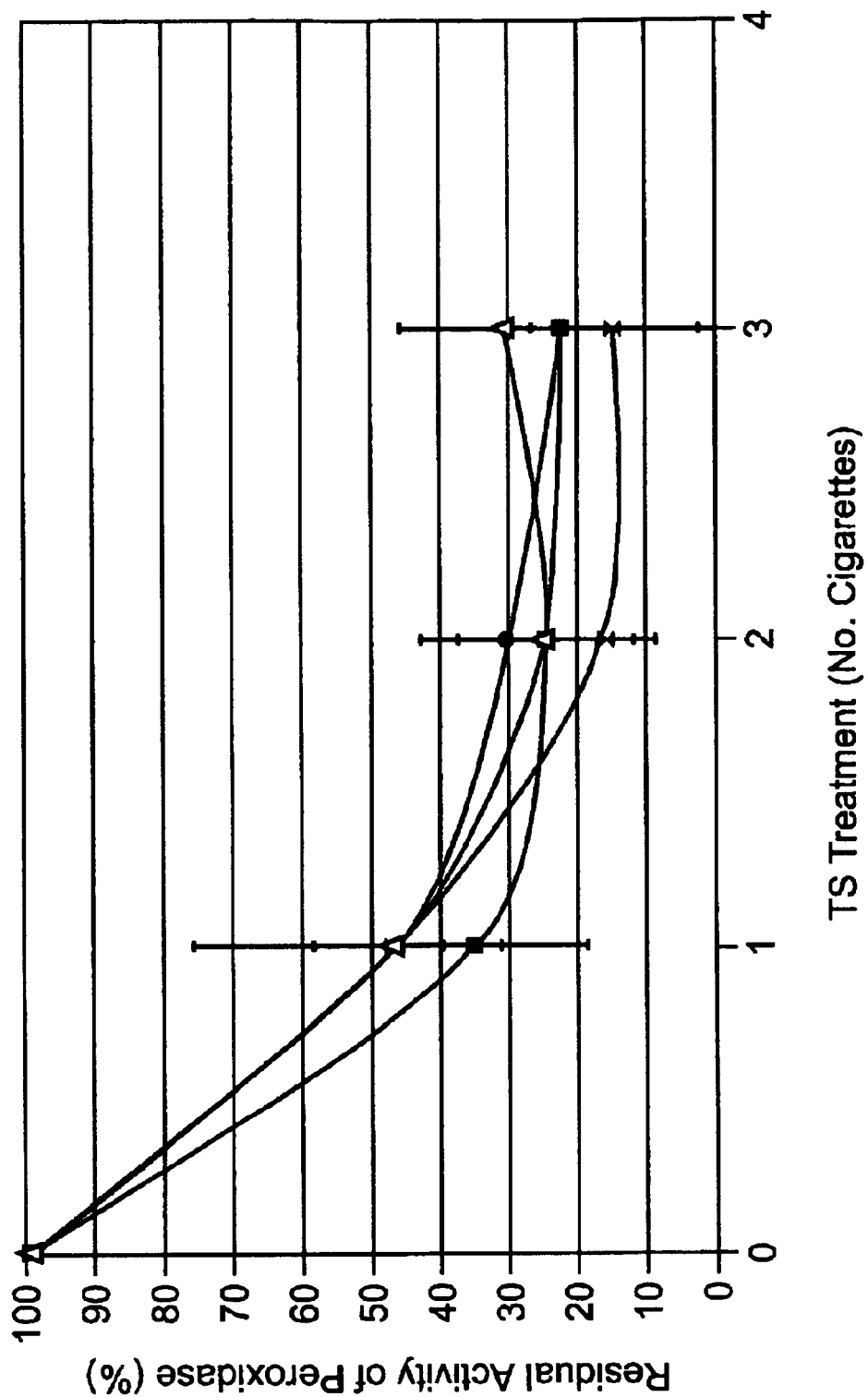
FIG. 9 is a data plot depicting the effect of GSH, deferoxamine (DES) and ascorbate on OPO activity in TS-treated saliva. Treatments: TS only (◇, n=4), TS+1 mM GSH (■, n=3), TS+1 mM deferoxamine (Δ, n=3), TS+1 mM ascorbate (X, n=3). Data plotted as mean±average OPO activity.
Figure 10:
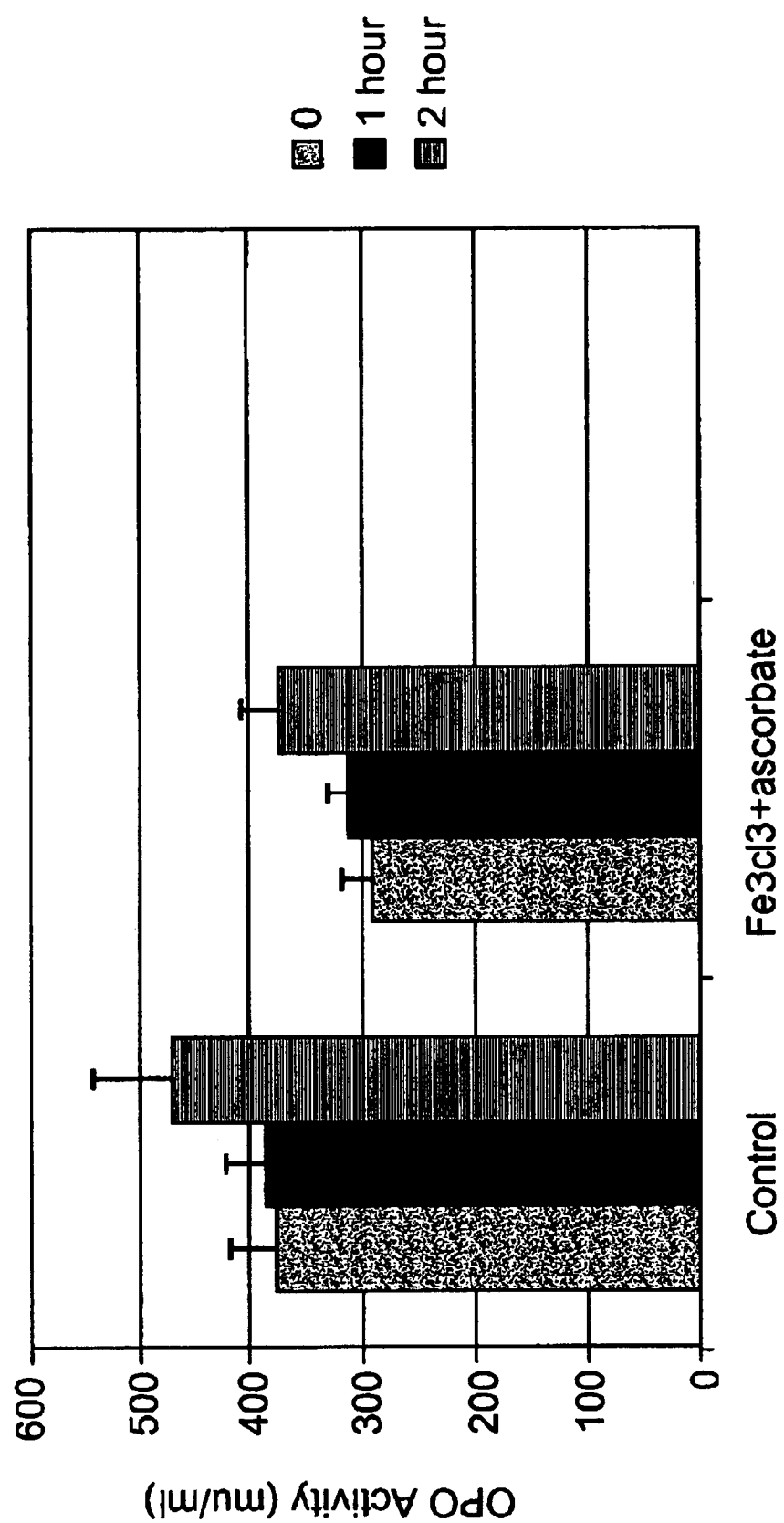
FIG. 10 is a data plot depicting the effect of 100 $\mu$M $FeCl_3$ or ascorbate on OPO activity in TS-treated saliva. Data points represent data plotted as mean±SD using saliva samples obtained from 3 subjects.

In the presence or absence of 1 mM of ascorbate or the antioxidants GSH or deferoxamine, loss of OPO activity in TS-treated saliva was found to be similar (FIG. 9) and exposure of saliva with 1 mM ascorbate or the oxidant 100 µM $FeCl_3$ for 2 h did not inhibit OPO activity (FIG. 10).

Figure 11:
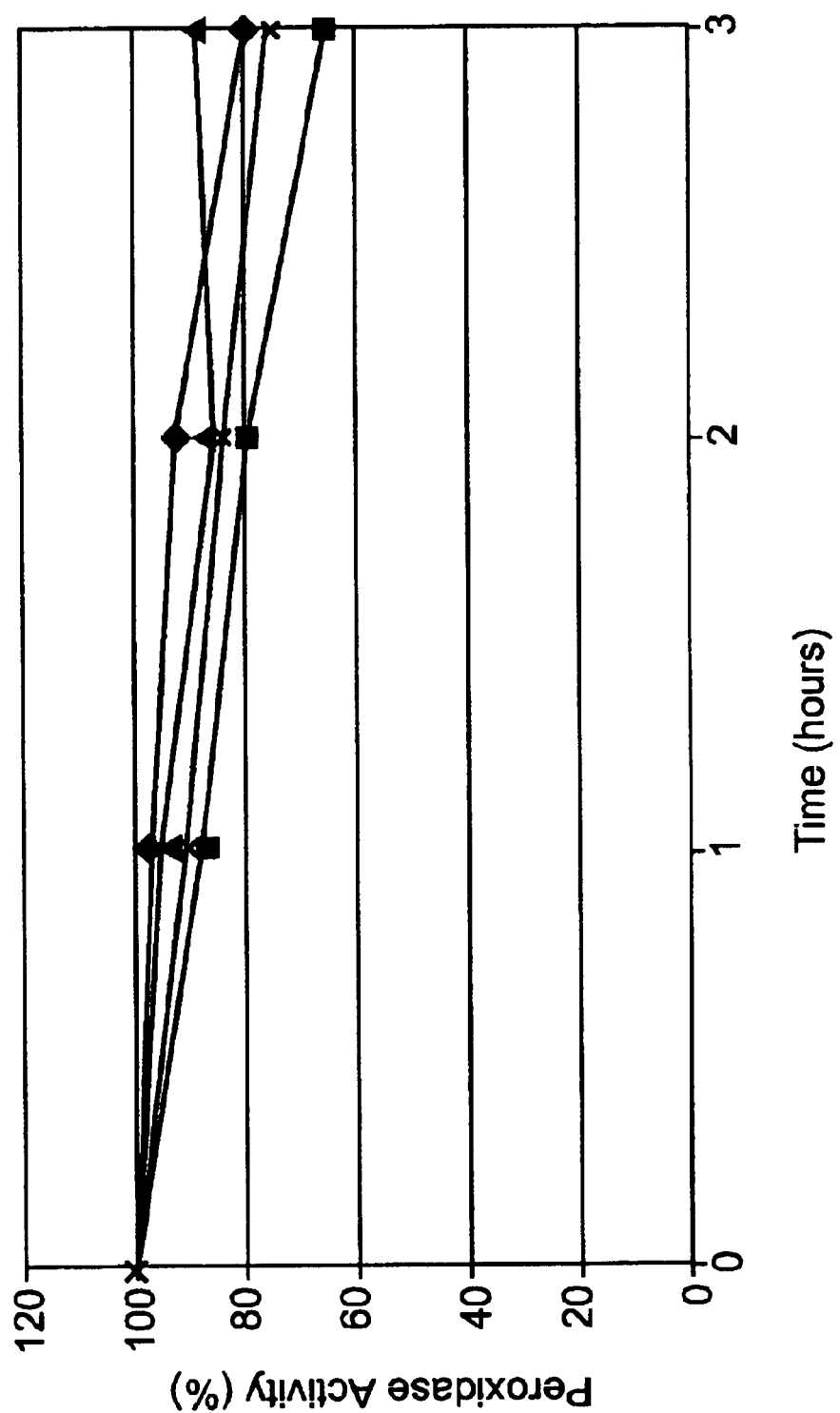
FIG. 11 is a data plot depicting the effect of purified aldehydes present in TS on OPO activity in saliva from 4–5 subjects. Treatment: exposure to air for 3 h (◇), 2 mM acetylaldehyde (●), 20 $\mu$M crotonaldehyde Δ), 80 $\mu$M acrolein (X).

In the presence of 2 mM acetylaldehyde, 80 µM acrolein, and 20 µM crotonaldehyde, major aldehydes present in TS, OPO activity in TS-treated saliva was unaffected (FIG. 11).

Figure 12:
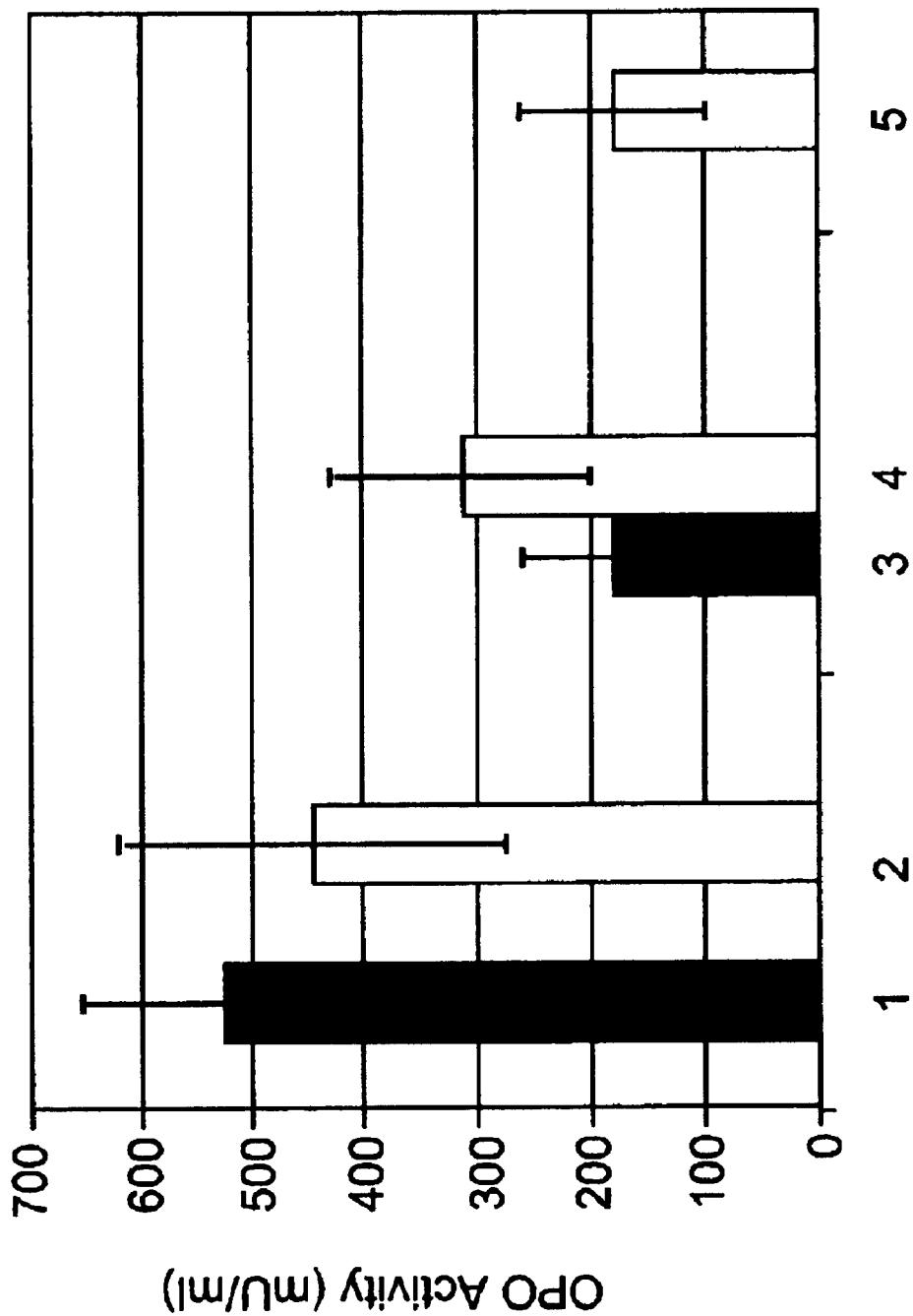
FIG. 12 is a histogram depicting the effect of 18 h of dialysis on OPO activity in TS-treated saliva having lost 68% of initial OPO activity levels. 1: control OPO activity in non-TS-treated saliva prior to [1] and following [2] dialysis, OPO activity in TS-treated saliva prior to [3] or following [4] dialysis and time-control following 18 h without dialysis [5].

Levels of OPO activity in TS-treated saliva having lost~68% of initial OPO activity were restored to 94% of initial levels following subsequent treatment with 18 h of dialysis (FIG. 12). Thus, loss of OPO activity in TS-treated saliva can be treated, presumably, via removal of low molecular weight molecules.

Figure 13:
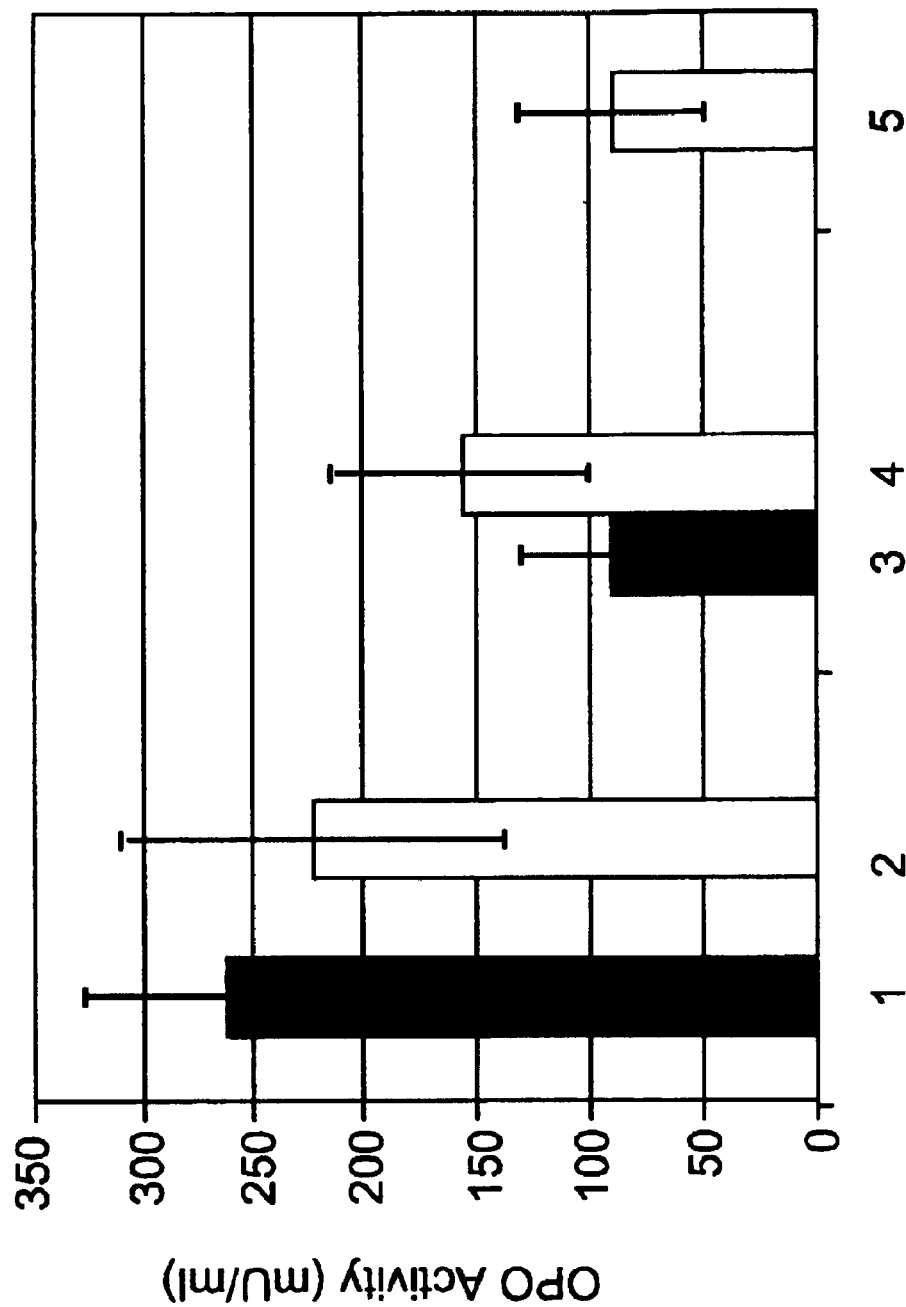
FIG. 13 is a histogram depicting recovery of OPO activity in saliva treated with KCN following 18 the of dialysis. OPO activity in non-TS-treated saliva prior to [1] or following [2] dialysis, OPO activity in saliva following 2 min KCN treatment prior to [3] or following [4] dialysis and time-control OPO activity in KCN-treated saliva following 18 h without dialysis.

Cyanide is a known inhibitor of heme peroxidase, and the gas-phase TS of various cigarette brands have been found to contain 2–233 µg of KCN (45). Thus, in order to test the hypothesis that dialysis treatment restores OPO activity in TS-treated saliva via removal of KCN, saliva samples were treated with 150 µM KCN and analyzed for OPO activity. This concentration of KCN was observed to cause a loss of ~65% of OPO activity after only 2 min of incubation, which loss was considerably reversed by dialysis (FIG. 13), thereby indicating that KCN is indeed capable of inhibiting OPO activity.

Hydroxocobalamin Prevents Tobacco Smoke-Associated Loss of Salivary Peroxidase: Since $CN^-$ ion was found to be involved in TS-associated loss of the OPO activity, the present inventors have attempted to provide a means of preventing such loss of OPO activity via the use of a $CN^-$ chelator.

Figure 14:
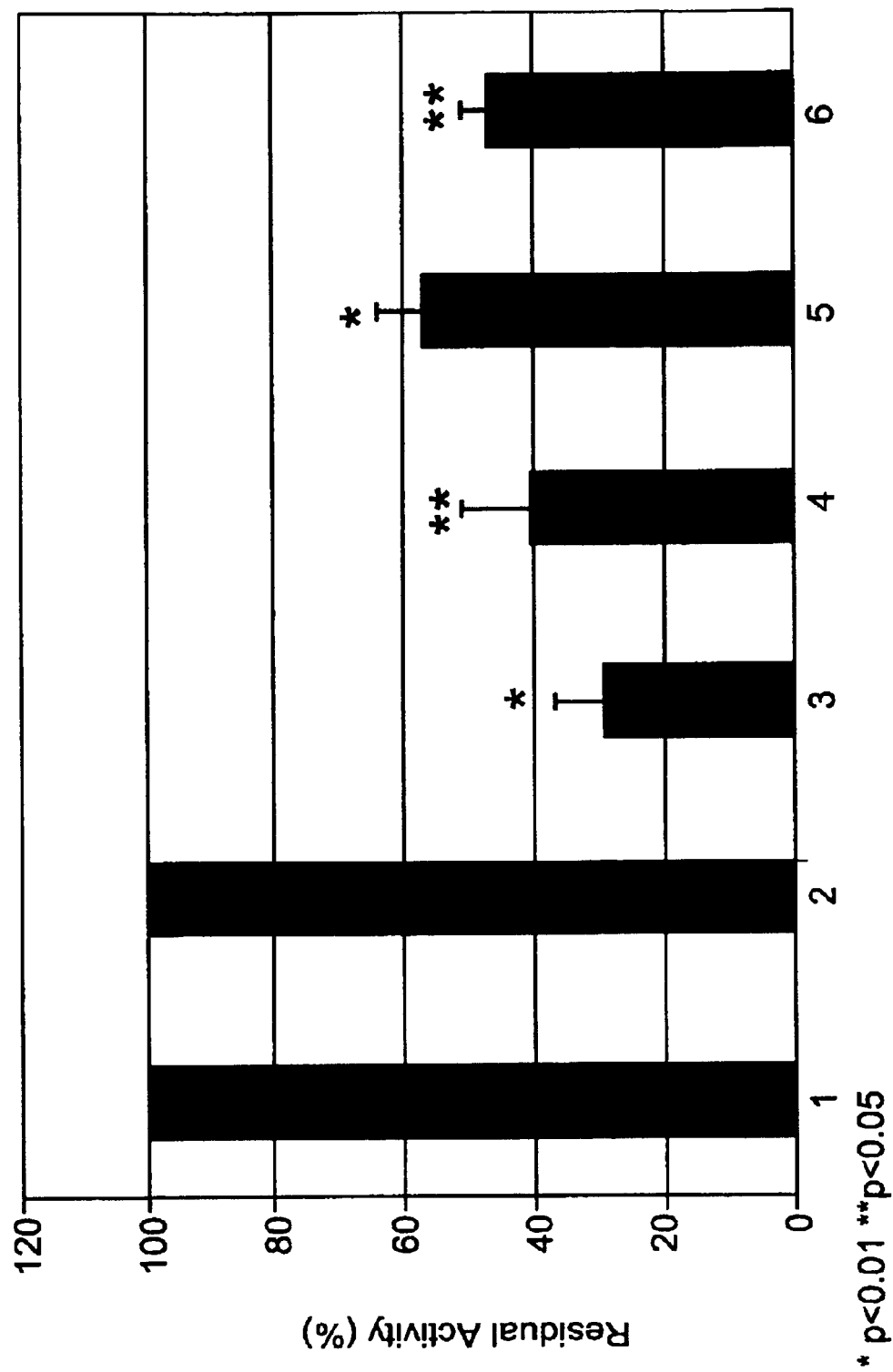
FIG. 14 is a histogram depicting OH—CO mediated prevention of OPO activity loss in saliva resulting from TS-treatment. OPO activity in non-TS-treated saliva in the absence [1] or presence [2] of 1 mM OH—CO (n=4), OPO activity in TS-treated saliva in the absence (n=4) [3] or presence of 0.5 mM OH—CO (n=3) [4], 1 mM OH—CO (n=3) [5] or 2 mM OH—CO (n=3) [6]. Each value represents data calculated as average±SD of results from 3–4 experiments using saliva from 3–4 subjects.
Figure 15:
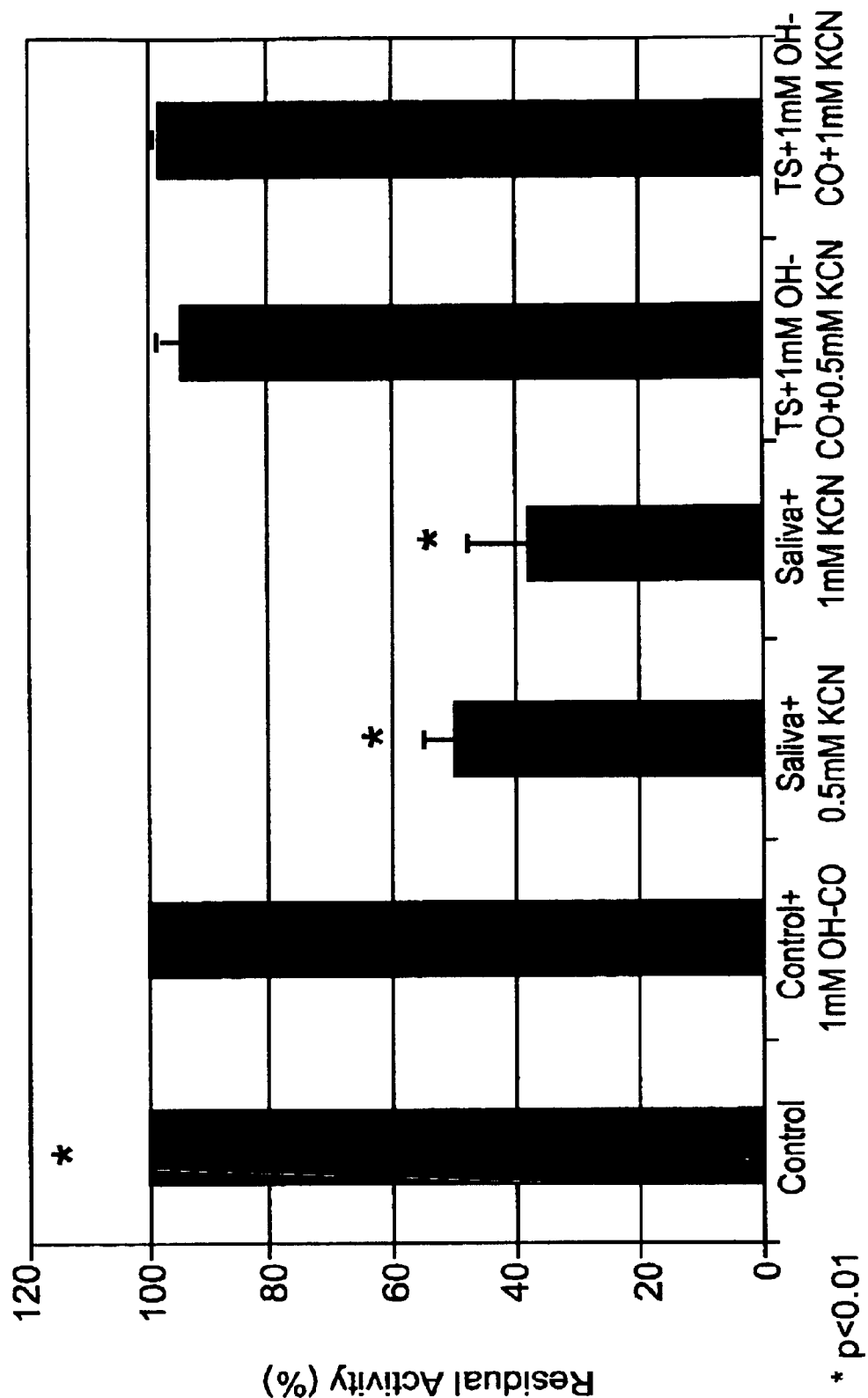
FIG. 15 is a histogram depicting OH—CO mediated prevention of OPO activity loss in KCN-treated saliva. Each value represents data calculated as average±SD of results from 3 experiments using saliva from 3 subjects.

Addition of increasing amounts of OH—CO, a known chelator of CN, was shown to prevent, to a significant extent, the loss of OPO activity saliva 40 min after treatment with TS (FIG. 14). Similarly, addition of 1 mM OH—CO to saliva treated for 2 min with 1 mM KCN was sufficient to completely prevent the KCN-associated loss of 40–60% of OPO activity (FIG. 15). Furthermore, preincubation of saliva with OH—CO could prevent both TS- and KCN-associated loss of OPO activity, indicating that cyanide indeed mediates TS-associated loss of OPO activity.

These results therefore indicate that, according to the present invention, OH—CO can be employed to effectively reduce or prevent the occurrence of diseases, such as malignancies of the aerodigestive tract, periodontitis and gingivitis associated with exposure to TS.

Example 2

The Antioxidants Deferoxamine and Glutathione Prevent Upper Aerodigestive Tract Lymphocyte Death Associated with Exposure to Tobacco Smoke Many diseases of the aerodigestive tract are associated with consumption of tobacco products or betel nut chewing. For example, oral SCC is the most common malignancy of the head and neck, having a high rate of morbidity and mortality. In as many as 90% of the cases, this cancer is induced by exposure of oral epithelial cells to tobacco products such as TS, or chewed betel nut. This exposure always occurs in the presence of saliva and presumably is induced by free radicals. Thus, the effects of TS on cells in the presence of saliva was examined, as described below.

Materials and Methods:

Mutagenic alterations of oral mucosal cells induced by TS occur in the presence of saliva (22, 23). Thus, in order to explore the interaction between TS and saliva on cells, intact cells were exposed to TS, alone or in the presence of saliva. Lymphocytes were employed since they are highly sensitive to oxidant injury.

Saliva Collection: Saliva was collected from healthy subjects, 3 males and 3 females ranging from 21–47 years of age, under non-stimulatory conditions in a quiet room during the morning between 8 am and noon. Saliva collection was performed at least 1 h after eating by spitting into a recipient for 10 minutes, as previously described (43). Following collection, saliva was immediately centrifuged at 800×g for 10 min at 4° C. to remove cells and cell debris and the resulting supernatant was used for biochemical analyses.

Lymphocyte Isolation: Blood from 10 consenting, healthy, non-smoking subjects, 5 males and 5 females ranging from 18–55 years of age, was drawn into EDTA-containing vacutainers. Lymphocytes were isolated by Ficoll-Hypaque (Sigma) gradient centrifugation according to the manufacturer's instructions and lymphocytes were suspended at $10^7$ cells/ml PBS (Beit-Ha'emek Industries, Israel), and used immediately in experiments.

Generation of Tobacco Smoke: Tobacco smoke was obtained from popular commercial cigarettes containing 14 mg of tar and 0.9 mg of nicotine ('Time' cigarettes, Dubek Ltd., Tel Aviv, Israel).

Treatment of Lymphocytes With TS in the Presence of Saliva: Exposure of lymphocytes to TS was carried out by attaching a Time cigarette (capable of removing particles>0.1 mm in diameter) in which the filter tip was removed to a Cambridge filter which was combined with a vacuum system to aspirate gas-phase TS inside sealed 250 ml flasks containing lymphocytes suspended in 12–15 ml PBS, as previously described (14, 15). A reproducible vacuum was created in the flask and upon application of vacuum for 5 s, 80–100 ml of TS from the lit cigarette was drawn into the flask. The chemical addititives GSH, NAC, deferoxamine, ascorbate (Asc), uric acid or $FeCl_3$ (Sigma) were added at the specified concentrations. Saliva treatment of lymphocytes was performed by suspending these in PBS supplemented with 30% (v/v) saliva. Following treatment with the TS of 0.5 cigarettes, flasks were incubated at 37° C. for 20 min in a metabolic shaker and subjected to a further 4 treatments with TS, as described above.

Measurement of Lymphocyte Survival: Lymphocyte viability was assessed by Trypan Blue exclusion assay.

Western Immunoblotting Analysis of Lymphocyte Protein Carbonylation: Lymphocytes were washed twice in PBS following treatment by centrifugation at 2,000 rpm for 2 minutes to remove saliva and other components of the incubation medium. Lymphocytes were then centrifuged at 14,000 rpm for 1 minute and lysed by sonication for 10 seconds in lysis buffer containing 20 mM Tris pH 7.4, 1 mM EGTA, 1 mM PMSF, 50 µM $NaVO_4$ and 50 mM NaF. Lysates were centrifuged at 14,000 rpm for 1 minute and supernatants were harvested for analysis. Carbonylation analysis was performed as described above.

Statistical Analysis: Results for statistical analysis were obtained from the control subgroup (lymphocytes in PBS) and from the various treatment subgroups. Means, SDs and SEMs were computed and results between the subgroups were analyzed and compared via one-way analysis-of-variance (46) using the Bonferroni Multiple-Comparison Test Model (47) to determine significant differences between computed means. The means between each pair of means was analyzed via T-test For Paired Differences and means between each two subgroups were compared via Two Sample T-test For Differences in Means (48).

Figure 16:
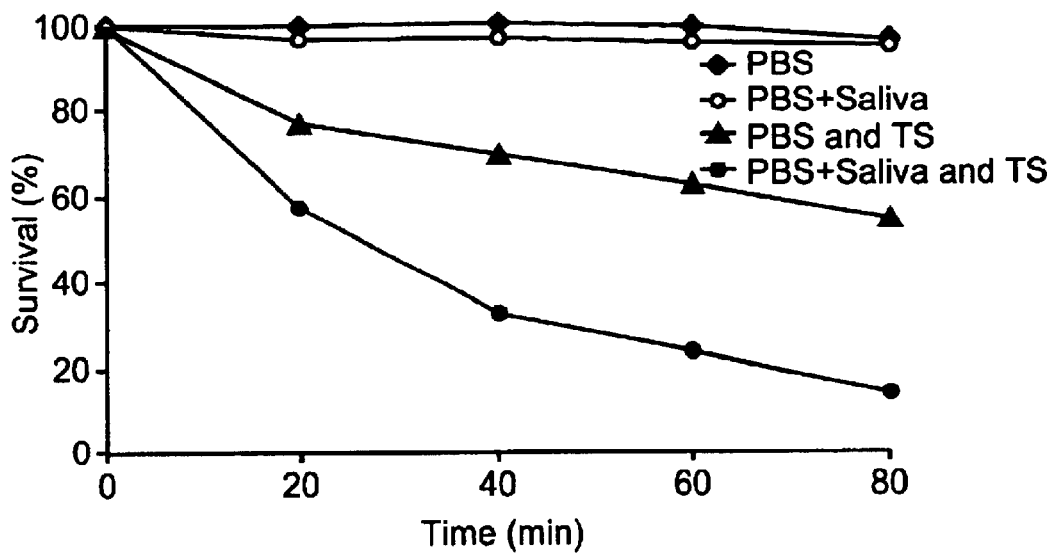
FIG. 16 is a data plot depicting death of lymphocytes incubated at 37° C. in the presence of TS and saliva.

Results:

During an 80 minute incubation of lymphocytes in PBS alone or in PBS supplemented with 30% (v/v) saliva, neither cell death nor protein carbonylation (FIGS. 16 and 17, respectively) occurred. Treatment of lymphocytes with TS in the absence of saliva resulted in time-dependent increases in cell death and protein carbonylation levels, peaking after 80 minutes with a death rate of 44% (p<0.01). Addition of saliva to lymphocyte suspensions during TS treatment synergistically potentiated the lethal effect of the TS, as demonstrated by an 86.2% (p<0.01) death rate and highly elevated protein carbonylation levels (FIGS. 16 and 17, respectively).

Figure 17:
FIG. 17 is a photograph of Western immunoblotting analysis depicting increased levels of protein carbonylation in lymphocytes treated with TS in the presence of saliva. Lane 1: incubation in PBS alone, Lane 2: incubation in the presence of saliva, Lane 3: incubation in PBS+TS, Lane 4: incubation with TS+saliva. Incubations were performed for 80 min at 37° C.
Figure 18:
FIG. 18 is a photograph of Western immunoblotting analysis depicting the effects of saliva and uric acid on lymphocyte protein carbonylation. Lane 1: incubation in PBS alone, Lane 2: incubation in the presence of saliva, Lane 3: incubation in the presence of 10 $\mu$M uric acid, Lane 4: incubation in the presence of 100 $\mu$M uric acid. Incubations were performed for 20 min at 37° C.

Addition of saliva to lymphocytes incubated for 80 minutes in PBS alone resulted in a mild reduction of protein carbonylation levels (FIG. 17). This was shown to be due to uric acid, the major non-enzymatic antioxidant in saliva (18, 28, 49), since addition of uric acid to the suspension medium instead of saliva led to reduced carbonylation levels (FIG. 18).

Supplementation of suspension medium with 1 mM ascorbate or 1 mM NAC did not alter the death rate of lymphocytes exposed to TS and saliva, whereas, addition of 1 mM GSH partially prevented this lymphocyte loss. At 20 and 80 minutes following TS and saliva treatment, the lymphocyte survival rates dropped to 57.1% and 13.8% respectively, whereas in the presence of GSH these survival rates were 93.4% (p=0.0001) and 24.3% (p=0.0037) respectively (FIG. 19).

Figure 19:
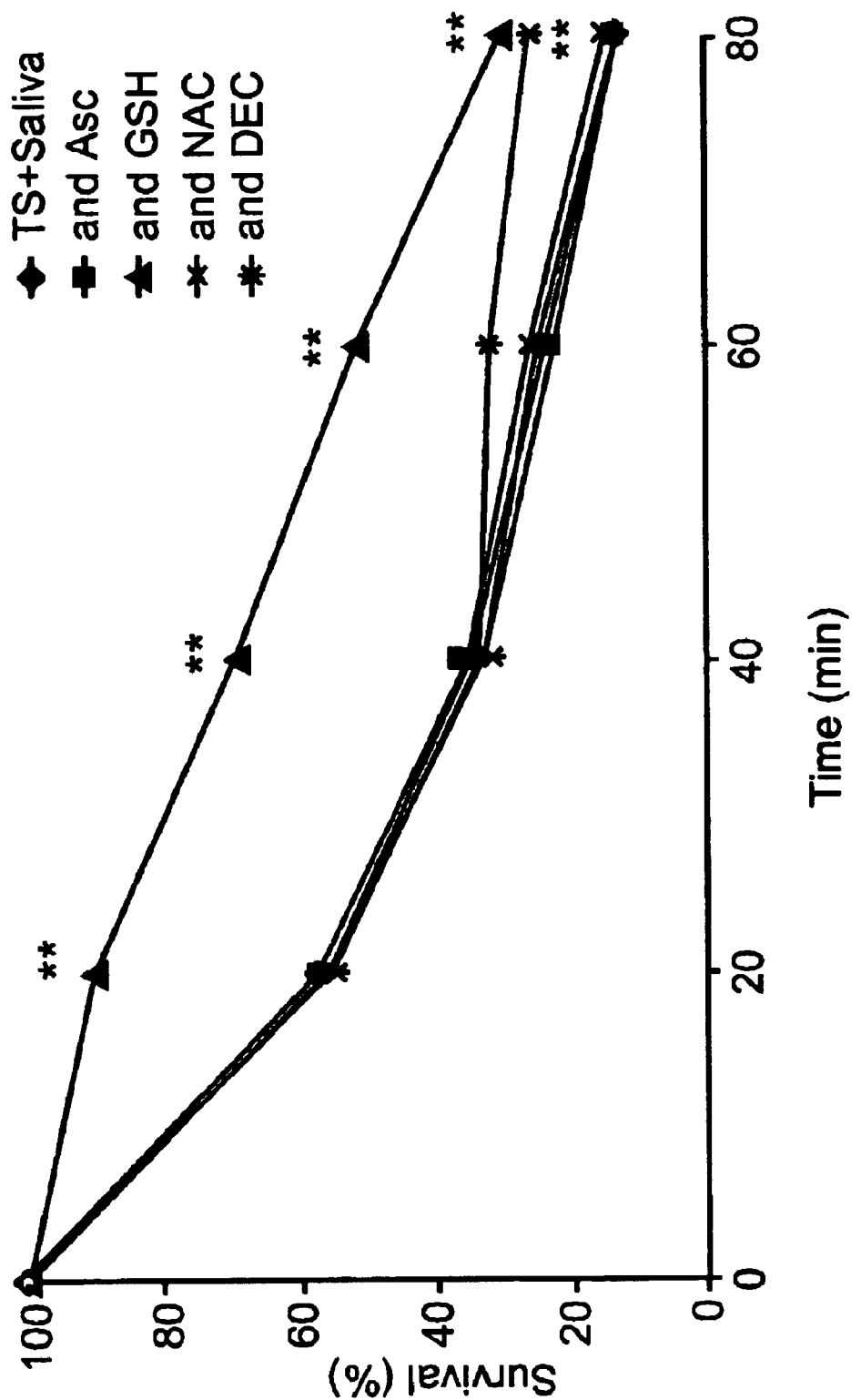
FIG. 19 is a data plot depicting the effects of various antioxidants; 1 mM GSH, 1 mM NAC (N-acetylcysteine)

Similarly to GSH treatment, addition of 1 mM deferoxamine significantly prevented lymphocyte death at 80 minutes, with a survival rate of 23.7% (p=0.005) (FIG. 19).

The unique protection offered by GSH at 20 minutes, in contrast to the lack of protection by all other antioxidants examined, was also demonstrated by assessing lymphocyte protein carbonylation levels (FIG. 20).

Role of Aldehydes: The demonstrated protection from TS+saliva-induced lymphocyte death by GSH led to the hypothesis that this effect was mediated by aldehydes associated with TS. Indeed, addition of various exogenous aldehydes known to be present in TS to lymphocytes suspended in PBS similarly led to cell death. Namely, in the presence of 80 µM acrolein, 20 µM crotonaldehyde or 2 mM acetaldehyde survival rates after 20 minutes were 63.3%, 80.3% and 93.6%, respectively, and at 80 minutes these death rates were 57.3%, 75.3% and 92.7%, respectively. This mimicking of the TS+saliva-induced lethality by exogenous aldehydes was further supported by protection from cell death being mediated by addition of GSH, similarly to GSH-mediated viability restoration in the presence of TS and saliva. Addition of GSH in the presence these aldehydes resulted in lymphocyte survival rates at 20 minutes of 93.3%, 82.3% and 93.3%, respectively and at 80 minutes these survival rates were 87.4%, 81.3% and 93.6%, respectively. As the survival rate of control lymphocytes was 95.7%, it was concluded that acetaldehyde does not play a role while acrolein, and to a slightly lesser degree crotonaldehyde, are the aldehydes causing cell death.

The pattern of injury induced by these aldehydes and the protection provided by GSH was similar in the concomitant levels of protein carbonylation (FIG. 21). However, in contrast to the profound synergistic effect demonstrated by treatment with saliva and TS, treatment with acrolein, the most potent thiol demonstrated, with saliva did not significantly alter the survival rates (57.9% and 66.4% respectively) and did not enhance carbonylation levels (FIG. 22). This ruled out the possibility that TS-saliva-based synergism involves TS-based aldehydes.

Role of Transition Metal Ions: The relatively moderate impact which exogenous aldehydes had on lymphocyte survival and the previously noted lack of related aldehyde-saliva synergy raised the possibility that there might be another mechanism mediating the injurious effects of TS on lymphocyte survival. The fact that deferoxamine had a similar protective effect as GSH pointed to the possible role of redox-active iron ions. In order to test this hypothesis, the role of redox-active iron was analyzed via an assay employing detection of redox-active iron mediated potentiation of ascorbate pro-oxidant activity. The role of redox-active iron ions was also analyzed using deferoxamine, a very potent iron chelator.

Addition of ascorbate to saliva-containing medium without exposure to TS resulted in reduction of the lymphocyte survival rate to 78% (p<0.01; FIG. 23, column 6). The modulatory role of redox-active iron was further demonstrated by addition of ascorbate to PBS containing iron but not saliva, as $FeCl_3$. This yielded similar results to those obtained by addition of ascorbate to saliva. Reduction of the lymphocyte survival rate to 77% was demonstrated (FIG. 23, Column 8), which reduction was totally prevented in the presence of deferoxamine (FIG. 23, Column 9).

Neither ascorbate nor deferoxamine were found to have any modulatory effect on the direct moderate lethal effect which TS had on lymphocytes in the absence of saliva (61% survival rate) (FIG. 24). This proved that redox-active iron ions did not originate from the TS but rather from the saliva, as described.

Protection from TS-Saliva Mediated Lymphocyte Death by GSH and Deferoxamine: Since the two major underlying mechanisms of lymphocyte loss identified above were based on the action of aldehydes and highly reactive free radicals mediated by redox-active iron, experiments aimed at protecting lymphocytes from both injurious mechanisms simultaneously were performed as follows.

Lymphocytes were exposed to TS and saliva in the presence of 1 mM GSH or both 1 mM GSH and deferoxamine at either low (1 mM) or high (5 mM) concentration. Both survival rates and carbonylation levels were examined after 20 and 80 minutes. Very significant protection against the lethal effect of TS was obtained by addition of 1 mM GSH and 5 mM deferoxamine to the saliva-containing medium prior to TS treatment of the lymphocytes. Whereas the survival rates of the non-protected lymphocytes were 57.2% and 14.4% at 20 and 80 minutes respectively, these rates climbed to 90.8% (p=0.0001) and 61.6%, respectively (Table 2). Furthermore, concomitant with this very significant improvement in survival rate, protein carbonylation levels dropped to nearly nil (FIG. 25, lanes 7, 8).

TABLE 2

Effect of GSH alone or in combination with 1 mM
deferoxamine on % survival of TS + saliva-treated lymphocytes.

| Treatment | 20 minute treatment | | | 80 minute treatment | | |
|---|---|---|---|---|---|---|
| | Mean | SEM | p | Mean | SEM | p |
| — | 57.2 | 3.7 | | 14.4 | 2.6 | |
| 1 mM GSH | 90.6 | 2.1 | 0.0001 | 28.8 | 3.4 | 0.0001 |
| 1 mM GSH + 1 mM deferoxamine | 92.2 | 1.6 | 0.0001 | 57.4 | 5.3 | 0.0001 |
| 1 mM GSH + 5 mM deferoxamine | 90.8 | 2.7 | 0.0001 | 61.6 | 3.0 | 0.0001 |

A comprehensive mechanism for the induction of disease by TS is suggested in which a new role is attributed to saliva losing its antioxidant capacity and becoming a potent prooxidant milieu in the presence of TS (FIG. 26). This mechanism is based on the results obtained in the current study as well as on the well-known observation that oral cancer mostly occurs in oral epithelial cells exposed to tobacco products (from TS or chewing betel nut) in the presence of saliva.

These results therefore indicate that GSH and deferoxamine, according to the present invention, can therefore be effectively employed to prevent or reduce diseases of the aerodigestive tract associated with cell death caused by tobacco consumption.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

REFERENCES CITED

1. Lippman S M, Hong W K. Molecular markers of the risk of oral cancer. N Eng J Med 2001;344:1323–6.
2. Nagler R M, Barak M, Ben-Aryeh H, Peled M, Filatov M, Laufer D. Early diagnostic and treatment monitoring role of Cyfra 21-1 and TPS in oral squamous cell carcinoma. Cancer 1999;35:1018–25.
3. Subdo J, Kildal W, Risberg B, Koppang H S, Danielsen H E, Reith A. DNA content as a prognostic marker in patients with oral leukoplakia. N Eng J Med 2001;344:1270–8.
4. Vokes E E, Weichselbaum R R, Lippma S M, Hong W K. Head and neck cancer. N Eng J Med 1993;328:184–94.
5. Epstein J B, Scully C. Assessing the patient at risk for oral squamous cell carcinoma. SCD Special Care in Dentistry 1997;17:120–8.
6. Holleb A I, Fink D J, Murphy G P. Textbook of Clinical Oncology. The American Cancer Society, 1991.
7. Ko Y C, Huang Y L, Lee C H, et al. Betel quid chewing, cigarette smoking and alcohol consumption related to oral cancer in Taiwan. J Oral Pathol Med 1995;24:450–3.
8. Piyathilake C J, Macaluso M, Hine R J, et al. Cigarette smoking, intracellular vitamin deficiency, and occurrence of micronuclei in epithelial cells of the buccal mucosa. Cancer Epidemiol Biomarkers Prev 1995;4:751–8.
9. Bross I D, Coombs J. Early onset of oral cancer among women who drink and smoke. Oncology 1976;33:136–9.
10. Model D. Smoker's face: an underrated clinical sign? Br Med J (Clin Res Ed). 1985 Dec 21–28;291(6511):1760.
11. Reznick A Z, Cross C E, Hu M-L, Suzuki Y J, Khwaja S, Safadi A, et al. Modification of plasma proteins by cigarette smoke as measured by protein carbonyl formation. Biochem J 1992;286:607–11.
12. Reznick A Z, Han D, Packer L. Cigarette smoke induced oxidation of human plasma proteins, lipids, and antioxidants; selective protection by the biothiols dihydrolipoic acid and glutathione. Redox Report 1997;3:169–174.
13. O'Neill C A, Halliwell B, Van der Vliet A, Davis P A, Packer I, Tristchler H, et al. Aldehyde-induced protein modifications in human plasma: protection by glutathione and dihydrolipoic acid. J Lab Clin Med 1994; 124:359–370.
14. Nagler R M, Lischinsky S, Diamond E, Drigues N, Klein Y, Reznick A Z. Effect of cigarette smoke on salivary proteins and enzyme activities. Arch Biochem Biophys 2000;379:229–36.
15. Nagler R M, Lischinsky S, Diamond E, Klein I, Reznick A Z. New insights into salivary lactate dehydrogenase of human subjects. J Lab Clin Med 2001;137:363–9.
16. Meucci E, Littarru C, Deli G, et al. Antioxidant status and dialysis: plasma and saliva antioxidant activity in patients with fluctuating urate levels. Free Rad Res 1998;29:367–76.
17. Moore S, Calder K A C, Miller N J, Rice-Evans C A. Antioxidant activity of saliva and periodontal disease. Free Rad Res 1994;21:417–25.
18. Nagler R M, Klein I, Zarzhevsky N, Drigues N, Reznick A Z. Characterization of the differentiated antioxidant profile of human saliva. Free Radic Biol Med 2001 (Provisionally accepted).
19. Nagler R M, Kitrossky N, Chevion M. Antioxidant activity of rat parotid saliva. Arch Otolarygol Head Neck Surg 1997; 123:989–93.
20. Pruitt K M, Kamau D N, Miller K, et al. Quantitative, standardized assays for determining the concentrations of bovine lactoperoxidase, human salivary peroxidase, and human myeloperoxidase. Anal Biochem 1990;191:278–86.
21. Azen E A. Salivary peroxidase activity and thiocyanate concentrations in human subjects with genetic variants of salivary peroxidase. Arch Oral Biol 1978;23:801–805.
22. Nagler R M, Marmary Y, Golan E, Chevion, M. Novel protection strategy against irradiation-induced and transition metal-mediated damage to salivary glands. Radiat Res 1998;142:271–6.
23. Nagler R M, Marmary Y, Fox P C, Baum B J, Har-El R, Chevion M. Irradiation-induced damage to the salivary glands: the role of redox-active iron and copper. Radiat Res 1997;147:468–75.
24. Jalil R A. Concentrations of thiocyanate and hypothiocyanate in the saliva of young adults. J Nihon Univ Sch Dent 1994;36:254–60.
25. Toljanic J A, Siddiqui A A, Patterson G L, Irwin M E. An evaluation of a dentifrice containing salivary peroxidase elements for the control of gingival disease in patients with irradiated head and neck cancer. J Prosthet Dent 1996;76:292–6.
26. Aune T M, Thomas E L. Accumulation of hypothiocyanate ion during peroxidase-catalyzed oxidation of thiocyanate ion. Eur J Biochem 1977;80:209–14.

27. Guven Y, Satman I, Dinccag N, Alptekin S. Salivary peroxidase activity in whole saliva of patients with insulin-dependent (type-1) diabetes mellitus. J Clin Periodontol 1996;23:879–81.
28. Grisham M B, Ryan E M. Cytotoxic properties of salivary oxidants. Am J Physiol 1990;258:115–21.
29. Dayan D, Hirshberg A, Kaplan I, et al. Experimental tongue cancer in desalivated rats. Oral Oncol 1997;33:105–9.
30. Nishioka H, Hishi K, Kyokane K. Human saliva inactivates mutagenicity of carcinogens. Mutat Res 1981;85:323–33.
31. Nair U J, Floyd R A, Nair J. et al. Formation of ROS and of 8-hydroxydeoxyguanosine in DNA in vitro with betel quid ingredients. Chem Biol Interact 1987; 63:157–169.
32. Knak R, Rutsatz K, Gocke R. Salivary investigations in oral lichen planus. J Dent Res 1998;77: Abstract #2783.
33. Irimi et al. Highly efficient tobacco smoke filter. U.S. Pat. No. 5,060,672. Oct. 29, 1991.
34. Pilotto et al. Dipeptide compounds having pharmaceutical activity and compositions containing them. U.S. Pat. No. 4,761,399, Aug. 2, 1988
35. Meister. Glutathione delivery system. U.S. Pat. No. 4,710,489, Dec. 1, 1987
36. Hersh. Antioxidant preparation. U.S. Pat. No. 5,922,346, Jul. 13, 1999
37. Hersh. Antioxidant gel for gingival conditions. U.S. Pat. No. 6,228,347, May 8, 2001
38. Hersh et al. Smoking products containing antioxidants. U.S. Pat. No. 5,829,449, Nov. 3, 1998
39. Waterbury. U.S. Pat. No. 3,667,478
40. U.S. Pat. No. 3,339,558
41. Barrows et al. Stabilized peroxide gels containing fluoride. U.S. Pat. No. 5,372,802, Dec. 13, 1994
42. Reznick A Z, Packer L. Oxidative damage to proteins: spectrophotometric method for carbonyl assay. Methods Enzymol 1994;233:1357–63.
43. Nagler R M, Marmary Y, Krausz Y, Chisin R, Markitziu A, Nagler A. Salivary gland dysfunction in human acute and chronic graft versus host disease (GVHD). Bone Marrow Transplant 1996;17:219–24.
44. van der Vliet, A.; Nguyen, M. N.; Shigenaga, M. K.; Eiserich, J. P.; Marelich, G. P.; Cross, C. E. Myeloperoxidase and protein oxidation in cystic fibrosis. Am. J. Physiol. Lung Cell. Mol. Physiol. 279:L537–L546; 2000.
45. Rickert, W. S.; Robinson, J. C.; Collishaw, N. E.; Bray, D. F. Estimating the hazards of "less hazardous" cigarettes. III. A study of the effect of various smoking conditions on yields of hydrogen cyanide and cigarette tar. J. Toxicol. Environ. Health 12:39–54; 1983.
46. Scheffe, H. The Analysis of Variance. New York: John Wiley & Sons. 1959
47. Hockberg Y, Tamhane A C. Multiple Comparison Procedures. New York: John Wiley & Sons. 1987.
48. Gosset W S (pseudo Student). On the probable error of a mean. Biometrika 1908;6:1–25.
49. Carlsson J. Salivary peroxidase: an important part of our defense against oxygen toxicity. J Ora Pathol 1987;16:412–416.

What is claimed is:

1. A filter comprising an agent being capable of reducing or preventing tobacco smoke-associated loss of peroxidase activity in the aerodigestive tract of a subject, the filter being designed and configured so as to enable release of said agent therefrom when an use by the subject wherein said agent is hydroxocobalamin.

2. The filter of claim 1, being designed and configured as a tobacco smoke filter.

3. The filter of claim 1, wherein said agent is capable of inactivating cyanide.

4. A filter comprising an agent being capable of reducing or preventing tobacco smoke-associated death of cells in the aerodigestive tract of a subject, the filter being designed and configured so as to enable release of said agent therefrom when in use by the subject, wherein said agent is an iron chelator.

5. The filter of claim 4, wherein said cells are lymphocytes.

6. The filter of claim 4, being designed and configured as a tobacco smoke filter.

7. The filter of claim 4, wherein said iron chelator comprises deferoxamine.

8. The filter of claim 4, wherein said agent is capable of preventing mediated toxicity.

9. A filter comprising an iron chelator being capable of reducing or preventing tobacco smoke-associated death of cells in the aerodigestive tract of a subject, the filter being designed and configured so as to enable release of said iron chelator therefrom when in use by the subject.

10. The filter of claim 9, wherein said cells are lymphocytes.

11. The filter of claim 9, being designed and configured as a tobacco smoke filter.

12. The filter of claim 9, wherein said iron chelator is deferoxamine.

13. A filter comprising an agent being capable of reducing or preventing tobacco smoke-associated loss of peroxidase activity in the aerodigestive tract of a subject, the filter being designed and configured so as to enable physico-chemical interaction between said agent and said tobacco smoke when in me by the subject, wherein said agent is hydroxocobalamin.

14. The filter of claim 13, being designed and configured as a tobacco smoke filter.

15. The filter of claim 13, wherein said agent is capable of inactivating cyanide.

16. A filter comprising an agent being capable of reducing or preventing tobacco smoke-associated death of cells in the aerodigestive tract of a subject, the filter being designed and configured so as to enable physico-chemical interaction between said agent and said tobacco smoke when in use by the subject, wherein said agent comprises an iron chelator.

17. The filter of claim 16, wherein said cells are lymphocytes.

18. The filter of claim 16, being designed and configured as a tobacco smoke filter.

19. The filter of claim 16, wherein said iron chelator comprises deferoxamine.

20. A filter comprising an agent being capable of reducing or preventing tobacco smoke-associated death of cells in the aerodigestive tract of a subject, wherein said agent includes an iron chelator and whereas the filter is designed and configured so as to enable physico-chemical interaction between said agent and said tobacco smoke when in use by the subject.

21. The filter of claim 20, wherein said cells are lymphocytes.

22. The filter of claim 20, being designed and configured as a tobacco smoke filter.

23. The filter of claim 20, wherein said iron chelator is deferoxamine.

* * * * *

UNITED STATES PATENT AND TRADEMARK OFFICE
CERTIFICATE OF CORRECTION

PATENT NO.    : 6,789,546 B2
DATED         : September 14, 2004
INVENTOR(S)   : Abraham Z. Reznick et al.

It is certified that error appears in the above-identified patent and that said Letters Patent is hereby corrected as shown below:

Column 27,
Line 64, change "an" to -- in --.

Signed and Sealed this

Eighteenth Day of January, 2005

JON W. DUDAS
*Director of the United States Patent and Trademark Office*